US012746379B2

(12) United States Patent
Dong et al.

(10) Patent No.: US 12,746,379 B2
(45) Date of Patent: Sep. 29, 2026

(54) FLEXIBLE LIGHT-INTEGRATED MICRONEEDLE THERAPY DEVICE

(71) Applicant: University of Central Florida Research Foundation, Inc., Orlando, FL (US)

(72) Inventors: Yajie Dong, Orlando, FL (US); Swaminathan Rajaraman, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 19/388,417

(22) Filed: Nov. 13, 2025

(65) Prior Publication Data

US 2026/0232978 A1 Aug. 13, 2026

Related U.S. Application Data

(60) Provisional application No. 63/758,004, filed on Feb. 13, 2025.

(51) Int. Cl.
*A61M 37/00* (2006.01)
*A61N 5/06* (2006.01)

(52) U.S. Cl.
CPC ....... *A61M 37/0015* (2013.01); *A61N 5/0616* (2013.01); *A61N 5/0622* (2013.01);
(Continued)

(58) Field of Classification Search
CPC .................. A61M 37/0015–2037/0061; A61M 2205/052; A61M 2205/053;
(Continued)

(56) References Cited

U.S. PATENT DOCUMENTS 6,931,277 B1 * 8/2005 Yuzhakov ......... A61M 37/0015 604/21
8,162,901 B2 * 4/2012 Gonnelli .............. A61B 17/205 604/246

(Continued)

FOREIGN PATENT DOCUMENTS

CN 111529920 A * 8/2020 .............. A61P 35/00
CN 114191700 A * 3/2022 ............. A61N 5/062

(Continued)

OTHER PUBLICATIONS

Paul O-Mahoney, Neil Haigh, Kenny Wood, C. Tom A. Brown, Sally Ibbotson, Ewan Eadie, A novel light source with tuneable uniformity of light distribution for artificial daylight photodynamic therapy, Photodiagnosis and Photodynamic Therapy, vol. 23, pp. 144-150 (Year: 2018).*

(Continued)

*Primary Examiner* — Bhisma Mehta
*Assistant Examiner* — Adam J. Cermak
(74) *Attorney, Agent, or Firm* — Anton J. Hopen; Trenam Law

(57) ABSTRACT

A wearable therapeutic device integrates a flexible light-emitting layer with a microneedle array for simultaneous phototherapy and transdermal drug delivery. The device includes a flexible substrate supporting a quantum dot light-emitting diode (QLED), organic light-emitting diode (OLED), or LED system, emitting therapeutic light at a wavelength optimized for photobiomodulation therapy (PBMT) and, in some embodiments, antimicrobial photodynamic therapy (aPDT). A biodegradable or dissolvable microneedle array penetrates the skin to deliver non-opioid analgesics, anti-inflammatory agents, biologics, or cosmetic formulations. A power supply and control module modulates light intensity, duration, and wavelength, while integrated sensors monitor treatment conditions. The combination of (Continued)

light therapy and microneedle-based drug delivery enhances treatment efficacy, precision, and patient compliance. This minimally invasive device is adaptable for neuropathic pain management, wound healing, skin rejuvenation, and other medical or cosmetic applications.

21 Claims, 7 Drawing Sheets

(52) U.S. Cl.
CPC ............... *A61M 2037/0023* (2013.01); *A61M 2037/0061* (2013.01); *A61M 2202/048* (2013.01); *A61M 2205/052* (2013.01); *A61N 2005/0627* (2013.01); *A61N 2005/0645* (2013.01); *A61N 2005/0653* (2013.01); *A61N 2005/0659* (2013.01); *A61N 2005/0663* (2013.01)

(58) Field of Classification Search
CPC .... A61N 2005/0645; A61N 2005/0653; A61N 2005/0659
See application file for complete search history.

(56) References Cited

U.S. PATENT DOCUMENTS

| | | | | |
|---|---|---|---|---|
| 10,967,119 | B1 * | 4/2021 | Bilal | A61M 5/14244 |
| 2002/0058936 | A1 * | 5/2002 | Avrahami | A61N 1/327 604/20 |
| 2002/0169411 | A1 * | 11/2002 | Sherman | A61B 5/15178 604/48 |
| 2003/0083645 | A1 * | 5/2003 | Angel | A61M 5/14248 604/890.1 |
| 2004/0236271 | A1 * | 11/2004 | Theeuwes | A61M 37/0015 604/47 |
| 2004/0260251 | A1 * | 12/2004 | Chang | B81C 1/00111 604/272 |
| 2008/0125743 | A1 * | 5/2008 | Yuzhakov | A61M 37/0015 604/506 |
| 2009/0042970 | A1 * | 2/2009 | Herschkowitz | A61M 37/0092 424/501 |
| 2009/0326447 | A1 * | 12/2009 | Joshi | A61K 31/00 604/82 |
| 2010/0121307 | A1 * | 5/2010 | Lockard | A61M 37/0015 604/117 |
| 2013/0046148 | A1 * | 2/2013 | Tathireddy | A61N 1/0551 600/300 |
| 2014/0276248 | A1 * | 9/2014 | Hall | A61N 1/30 604/20 |
| 2016/0339223 | A1 * | 11/2016 | Scherr | A61B 5/150282 |
| 2019/0015650 | A1 * | 1/2019 | Jaklenec | A61M 37/0015 |
| 2019/0224462 | A1 * | 7/2019 | Cho | A61M 37/0015 |
| 2021/0060323 | A1 * | 3/2021 | Rape | A61M 37/0015 |
| 2021/0205632 | A1 * | 7/2021 | Xu | A61N 5/0601 |
| 2022/0105328 | A1 * | 4/2022 | Mir | A61M 37/0015 |
| 2023/0173193 | A1 * | 6/2023 | Evjensvold | A61M 5/3295 604/173 |
| 2024/0228570 | A9 * | 7/2024 | Neumann | A61K 35/15 |
| 2024/0252452 | A1 * | 8/2024 | Pathak | A61K 31/7036 |
| 2024/0350785 | A1 * | 10/2024 | Shechter | A61M 37/0015 |
| 2025/0152929 | A1 * | 5/2025 | Falo, Jr. | A61M 37/0015 |
| 2025/0229068 | A1 * | 7/2025 | Qiao | A61M 37/0015 |
| 2026/0014359 | A1 * | 1/2026 | Koma | A61K 9/0021 |
| 2026/0097198 | A1 * | 4/2026 | Cho | A61M 37/0015 |

FOREIGN PATENT DOCUMENTS

| | | | | |
|---|---|---|---|---|
| CN | 114209976 B | * | 4/2023 | A61K 9/7023 |
| CN | 116139413 A | * | 5/2023 | A61N 5/062 |
| CN | 117414349 A | * | 1/2024 | A61K 9/0024 |
| CN | 118526724 A | * | 8/2024 | A61F 13/122 |
| KR | 20240154109 A | * | 10/2024 | A61M 5/46 |
| WO | WO-2018053017 A1 | * | 3/2018 | A61B 5/291 |

OTHER PUBLICATIONS

Kim, M.M. and Darafsheh, A., Light Sources and Dosimetry Techniques for Photodynamic Therapy, Photochem. Photobiol., 96: 280-294 (2020; available at doi.org/10.1111/php.13219). (Year: 2020).*

Kim, M.M. and Darafsheh, A., Light Sources and Dosimetry Techniques for Photodynamic Therapy, Photochem. Photobiol., 96: 280-294 (Year: 2020).*

Akasov et al., Nanoparticle enhanced blue light therapy, Advanced Drug Delivery Reviews 184, 2022, pp. 1-17.

Li et al., A wearable and stretchable dual-wavelength LED device for home care of chronic infected wounds, Nature Communications, 2024, 15:9380, pp. 1-20.

Zhao et al., Miniaturized all-in-one microneedle device for point of care light therapy, Flexible Electronics, 2024, 8:32, pp. 1-11.

* cited by examiner

Fig. 1A
Fig. 1B
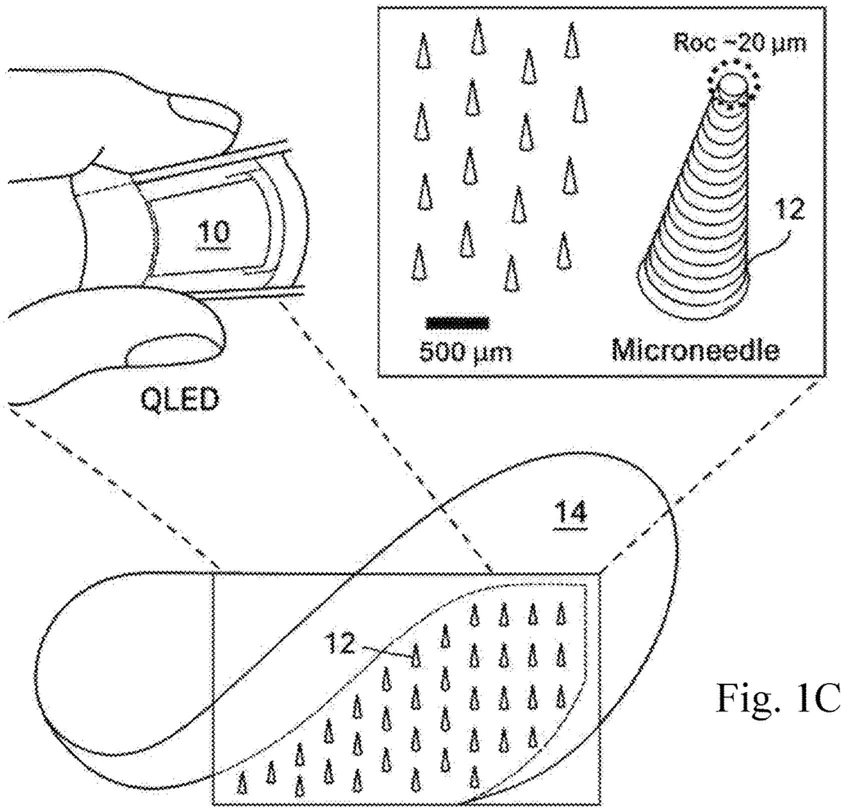
Fig. 1C
Fig. 1D
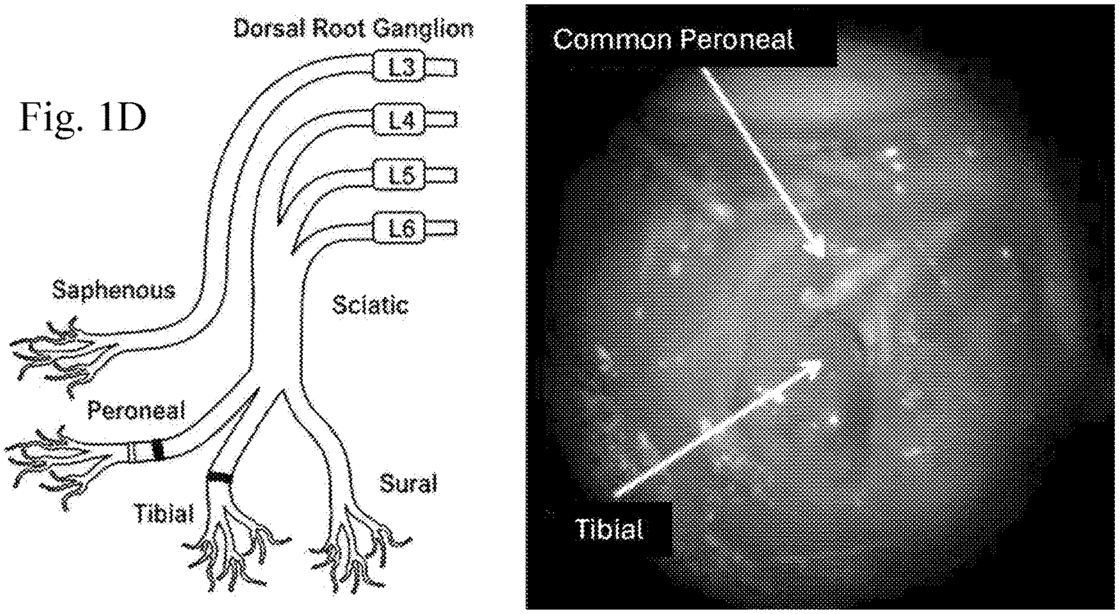
*In Vivo* Spared nerve injury rat pain model

FLEXIBLE LIGHT-INTEGRATED MICRONEEDLE THERAPY DEVICE

PRIORITY CLAIM

This application claims the benefit of U.S. Provisional Patent Application No. 63/758,004, filed on Feb. 13, 2025, entitled "Flexible Light-Integrated Microneedle Therapy Device," the entire disclosure of which is hereby incorporated by reference in its entirety.

FEDERALLY SPONSORED RESEARCH OR DEVELOPMENT

This invention was made with Government support under Grant No. W911NF22P0018 awarded by the United States Department of Defense. The government has certain rights in the invention.

BACKGROUND OF THE INVENTION

Field of the Invention

This invention relates, generally, to wearable therapeutic devices for medical and cosmetic treatments. More specifically, it relates to a flexible, light-emitting device integrated with a microneedle array for simultaneous photobiomodulation therapy and transdermal drug delivery.

Brief Description of the Prior Art

Microneedle Technology in Transdermal Drug Delivery. Microneedle (MN) technology has emerged as an innovative method for transdermal drug delivery, offering an alternative to traditional methods such as oral administration, injections, and passive diffusion through the skin. Unlike hypodermic needles, microneedles are designed to minimize pain and tissue damage, making them a promising approach for delivering pharmaceuticals, biologics, and cosmetic agents. These microneedles are typically fabricated from materials such as polymers, silicon, or metals and can be either solid, coated, hollow, or dissolvable, depending on the intended application.

One of the key advantages of microneedle-based drug delivery is its ability to bypass the stratum corneum, the outermost barrier of the skin, enabling more efficient and controlled absorption of active ingredients. This has made microneedle technology attractive for applications such as vaccination, pain management, cosmetic treatments, and systemic drug administration.

Despite its advantages, conventional microneedle technology faces limitations that hinder its widespread adoption. Many microneedle systems require additional delivery mechanisms to enhance drug penetration and effectiveness. Passive diffusion alone is often insufficient for certain formulations, particularly large-molecule biologics. Moreover, the rate of drug absorption can be inconsistent, requiring prolonged application times or multiple treatments. This has led researchers to explore complementary techniques, such as heat, ultrasound, and light therapy, to improve drug delivery outcomes.

Light Therapy and Photobiomodulation in Medical Treatments. Light therapy, also known as photobiomodulation therapy (PBMT), has been widely studied for its ability to modulate cellular function, promote tissue repair, and reduce inflammation. This therapy relies on specific wavelengths of light, typically in the red and near-infrared spectrum, to stimulate biological processes. It has been used in applications such as wound healing, pain management, dermatological treatments, and neurological rehabilitation.

Traditional light therapy devices utilize LEDs, lasers, or fiber-optic systems to deliver targeted illumination. While these devices have demonstrated therapeutic benefits, they also come with significant drawbacks. Many LED and laser-based light therapy systems are rigid and bulky, limiting their ability to conform to irregular body surfaces. Additionally, inconsistent light distribution across the treatment area can result in variable therapeutic outcomes. Some systems require external cooling mechanisms to manage heat output, adding complexity and reducing patient comfort.

Another limitation of existing photobiomodulation devices is that they operate independently of drug delivery mechanisms. This separation often necessitates sequential treatment sessions, increasing the overall treatment time and requiring patients to use multiple devices. This lack of integration limits synergistic effects that could enhance therapeutic outcomes, particularly in conditions where both drug administration and light therapy could work together to improve efficacy.

Recent flexible-QLED studies report emission tuned to photosensitizer absorption, physiologic surface temperatures (<41° C.), and improved operating lifetime, supporting the suitability of spectrally matched flexible emitters for wearable aPDT embodiments disclosed here.

Deficiencies in the Current State of the Art

Separation of Modalities. Current medical and cosmetic treatments frequently require separate devices for microneedle drug delivery and light therapy, leading to longer treatment durations and reduced patient adherence. Patients undergoing phototherapy for skin rejuvenation, wound healing, or pain relief must complete multiple sessions before or after receiving transdermal drug applications, making the process cumbersome. In clinical settings, managing multiple treatment devices increases cost and complexity, requiring additional training for healthcare providers.

Limited Synergy Between Light Therapy and Drug Absorption. Research has shown that light exposure can enhance skin permeability and increase drug absorption, yet current devices fail to leverage this potential synergy. Conversely, microneedle penetration can improve light penetration into deeper skin layers, making it possible to optimize therapeutic effects. However, conventional systems do not combine these functionalities, missing opportunities for enhanced treatment efficacy.

Rigid and Inflexible Designs. Most light therapy systems are designed as handheld or stationary devices, making them difficult to use on curved or irregular surfaces. Traditional LED-based systems lack flexibility and adaptability, limiting their effectiveness in areas such as joints, facial contours, or sensitive body regions. Similarly, microneedle patches, while conformable, do not incorporate flexible light sources, reducing their potential for customized, patient-specific therapy.

Higher Costs and Increased Complexity. The need for separate medical devices for microneedle-based drug delivery and light therapy results in higher costs for both patients and healthcare providers. Clinical procedures that involve two independent treatment modalities require additional equipment, maintenance, and procedural steps, making them less efficient and more resource-intensive. This complexity can also lead to lower compliance rates, particularly in home-use or wearable applications where patients must operate multiple devices correctly.

Inconsistent Drug Absorption and Light Exposure. In current systems, microneedle drug delivery is not optimized for simultaneous light exposure, leading to inconsistent drug diffusion and light absorption rates. Some therapeutic compounds require controlled release timing for maximum efficacy, which cannot be synchronized with standalone light therapy devices. Additionally, the depth of microneedle penetration affects how light interacts with tissues, but traditional phototherapy devices are not designed to accommodate these variations.

Limited Wearability and Home-Use Solutions. The current landscape of light therapy and microneedle-based treatments lacks integrated, wearable solutions. Existing light therapy systems require users to hold or position devices manually, limiting their practicality for extended treatment durations. Microneedle patches, while promising, lack real-time monitoring and control mechanisms, making it difficult to adjust treatment parameters dynamically. A lack of smart features also prevents patients from receiving feedback on treatment effectiveness, further reducing engagement and adherence.

Need for an Integrated Solution.

The limitations outlined above highlight the need for an advanced, multifunctional therapeutic system that combines microneedle-based drug delivery with flexible, wearable light therapy. An ideal solution should address the separation of modalities, enhance therapeutic synergy, improve flexibility, reduce costs, and simplify treatment procedures. By overcoming these deficiencies, a new generation of integrated, patient-friendly medical devices could significantly enhance efficacy, patient compliance, and overall treatment outcomes.

BRIEF SUMMARY OF THE INVENTION

The present disclosure describes a wearable therapeutic system configured to combine photobiomodulation therapy with microneedle-mediated transdermal drug delivery in a single flexible and modular platform. This system addresses longstanding technical challenges inherent in deploying light-based therapy and microneedle patches as standalone solutions. By integrating these functionalities, the device achieves a synergistic effect that enhances treatment outcomes, reduces the total number of treatment sessions, and provides automated feedback control to maintain optimal therapeutic conditions. The following detailed description sets forth the structural and operational principles of the system, alongside potential applications that encompass pain management, dermatological interventions, wound healing, and cosmetic treatments.

The device incorporates a flexible substrate, chosen to permit intimate contact with the skin while supporting electronic, photonic, and microneedle components. The substrate may be constructed from polymeric materials such as polyethylene terephthalate, polyethylene naphthalate, polydimethylsiloxane, or other polymer composites. The choice of material is influenced by factors such as optical clarity (where needed), mechanical robustness, biocompatibility, and tolerance for repeated flexion. Once prepared, the substrate can accommodate a light-emitting layer consisting of quantum dot light-emitting diodes (QLEDs), organic light-emitting diodes (OLEDs), or arrays of conventional light-emitting diodes (LEDs). Each of these light-emitting technologies has distinctive benefits for phototherapeutic applications. For instance, QLEDs provide high color purity and wavelength tunability, OLEDs permit thin and flexible illumination surfaces, and LEDs can be manufactured cost-effectively at scale. Regardless of the chosen light source, this layer is configured to emit light at wavelengths that stimulate photobiological processes in tissues.

Experimental and clinical literature suggests that certain wavelengths in the red and near-infrared spectral range can promote mitochondrial activity, modulate inflammatory processes, and enhance tissue regeneration. The invention capitalizes on these findings. In some embodiments, light output may be restricted to approximately 630 to 660 nm, a region shown to influence cytochrome c oxidase activity and thereby accelerate cellular repair mechanisms. In more comprehensive iterations, the device can cover a broader set of wavelengths spanning visible red light (roughly 600 to 670 nm), near-infrared wavelengths (about 780 to 940 nm), and extended near-infrared light up to approximately 1064 nm. Such coverage is intended to match absorption windows for various chromophores, enabling superficial or deeper therapeutic actions. For example, red wavelengths of around 630 to 670 nm are known to be well-suited for managing superficial soft-tissue injuries and improving skin health, while near-infrared wavelengths of 800 to 900 nm can penetrate deeper into muscle or nerve tissue, aiding in the treatment of neuropathic pain or deeper wound sites. In still other variants, the device may include emission bands in shorter wavelengths (e.g., in the blue or green range) for specific dermatological or antibacterial applications, although the principal emphasis of the device remains on red-to-near-infrared photobiomodulation due to its broad applicability in pain and wound management.

In aPDT embodiments, the light-emitting layer is configured to emit at one or more wavelengths matched to an onboard or co-administered photosensitizer. In some embodiments, methylene blue (MB)-matched emission is provided near about 650-660 nm; in other embodiments, PpIX Q-band emission is provided near about 630-635 nm and optionally a Soret band near about 405 nm. For Ce6 (chlorin e6) and ICG (indocyanine green), emission near about 660-670 nm and 780-820 nm, respectively, can be provided. The system can alternate or combine wavelengths in a programmable sequence to manage multi-peak activation, photobleaching, and heat while maintaining homogeneous fluence over the treated area.

A microneedle array is disposed on or integrated with the light-emitting layer, typically fabricated from dissolvable or biodegradable materials such as polyethylene glycol diacrylate (PEGDA), polyvinylpyrrolidone (PVP), or silk fibroin. The microneedles may be produced via micromolding, 3D printing using stereolithography, or digital light processing techniques. The manufacturing process must achieve consistent tip sharpness and uniform geometry, allowing the microneedles to painlessly breach the stratum corneum and deposit active pharmaceuticals in a reproducible manner. Dissolvable polymer microneedles are especially suitable when avoiding sharps waste is a priority; once the drug payload has diffused into the tissue, the microneedles gradually degrade, leaving no solid residue. Because the drug molecules are placed closer to the vasculature and peripheral nervous system, systemic exposure is typically minimized in comparison to oral or intravenous delivery routes. This targeting is especially relevant for neuropathic pain, where localized administration of analgesics reduces the likelihood of systemic side effects.

In certain embodiments, a reservoir is placed in fluid communication with the microneedle array to allow sustained or on-demand drug release. For pain management, the reservoir can contain non-opioid analgesics such as ropivacaine or anti-inflammatory agents such as meloxicam. Dissolvable microneedles can encapsulate these agents internally, or the reservoir can feed the microneedles over time, maintaining drug concentrations in the local tissue for extended periods. This design may also incorporate pH-sensitive, thermosensitive, or photosensitive release triggers that control when and how quickly the active agent diffuses through the microneedle channels. These triggers can synergize with the photobiomodulation aspect of the invention: the localized heat or enhanced blood flow from light therapy can facilitate increased diffusion or dissolution rates, thereby amplifying the therapeutic effect. The choice of microneedle geometry (length, tip diameter, and spacing) is another adjustable parameter, permitting device adaptation for different body sites and therapy objectives. Longer needles and narrower tips may be beneficial for deeper tissue infiltration, whereas shorter needles may suffice for superficial skin rejuvenation protocols.

The microneedle array can encapsulate, coat, or otherwise carry a photosensitizer for aPDT. In some variants, a reservoir feeds a photosensitizer solution or hydrogel to the microneedles for sustained or on-demand delivery. Photosensitizer loading can be configured for rapid release over minutes or for controlled release over hours, including stimulus-responsive release triggered by temperature, pH, hydration, or illumination.

For closed-loop control, sensors can monitor a photobleaching signal (change in photosensitizer absorption or fluorescence), diffuse reflectance, local temperature, and indicators of oxygenation. The control module can adjust irradiance, duty cycle, wavelength selection, or treatment duration responsive to these signals, and can prompt the user to reposition the device or increase contact pressure when incomplete microneedle penetration is detected.

A power supply and control module is operably connected to the light-emitting layer, thereby allowing automated or user-directed modulation of the light therapy parameters. This module may include a rechargeable battery encased within a flexible enclosure, ensuring that the overall device maintains comfortable wearability for extended treatment sessions. Many advanced variants of the control system can measure real-time device metrics and environmental factors. For example, integrated sensors can record the local skin temperature, impedance, or optical backscatter, enabling the system to detect the microneedle array's penetration depth and confirm that the needles have formed adequate microchannels. Other sensors track the total delivered light dose, verifying that target fluence levels are achieved. The control module can employ such feedback to alter the intensity or duration of illumination and, where applicable, regulate the rate of drug release from the reservoir. This adaptive capability addresses the inter-patient variability that often hinders standardized clinical outcomes. In practical terms, a user or clinician can set broad treatment parameters, and the module refines them in real time based on sensor data, ensuring safer and more consistent therapy.

Sensors can monitor aPDT-relevant parameters such as local reflectance, fluorescence, photobleaching kinetics of the photosensitizer, oxygenation, temperature, and tissue impedance. The control module can adjust irradiance, duty cycle, and wavelength selection in response, and may prompt the user to reposition or increase contact pressure if incomplete microneedle penetration is detected.

The disclosed system is designed for multiple medical and cosmetic uses. Among medical applications, neuropathic pain management is a prominent target. Many non-opioid alternatives are being sought to mitigate the risks of addiction, and microneedle-based transdermal delivery of local anesthetics or nonsteroidal anti-inflammatory drugs provides an avenue for sustained local treatment. Coupling this delivery approach with photobiomodulation can further reduce inflammatory markers in both superficial and deeper tissues. The near-infrared component of the light output may reach subdermal or perineural regions that mediate chronic pain. In experimental models, photobiomodulation in the red or near-infrared range can modulate the phenotype of inflammatory cells, shifting them from pro-inflammatory (M1) to anti-inflammatory (M2). This effect, in conjunction with localized drug release, shows potential for lowering pain scores and inflammation more effectively than standalone methods.

Beyond analgesia, the device is suitable for wound healing and tissue regeneration. Light in the red-to-near-infrared window can accelerate fibroblast proliferation, collagen synthesis, and angiogenesis. By delivering growth factors, antimicrobial agents, or other bioactive formulations via microneedles, the device creates an environment conducive to rapid wound closure and lower infection rates. These outcomes are particularly pertinent in diabetic ulcers or chronic wounds resistant to conventional therapies. Another related field is dermatological and cosmetic enhancement, where the device can facilitate skin rejuvenation, scar minimization, and pigmentation correction. In these contexts, the microneedle array can deliver peptides, retinoids, or skin-lightening agents directly into the dermis, while concurrent light exposure improves local circulation and metabolic activity. Clinical or at-home users benefit from a simplified regimen where a single patch can be applied to the target site for an appropriate duration, sparing them from multiple visits to specialized therapy centers.

For infected or at-risk wounds, the device can deliver a photosensitizer by microneedles and apply wavelength-matched light to perform aPDT over the target area. This may be used for refractory or multidrug-resistant infections and can be combined with PBMT to support tissue repair. In some examples, emission-matched F-QLED operation has achieved multi-log reductions of pathogenic bacteria under physiologic surface temperature caps, supporting MDR wound applications contemplated herein.

The ability to produce a flexible substrate is central to this invention's advantage in terms of conformability and wearability. Traditional laser-based phototherapy systems typically require a rigid device or specialized clinician skills. By contrast, the present system can be used passively at home, with the user wearing it as they move about. The microneedles are generally less than one millimeter in length, minimizing the risk of pain or bleeding, and the flexible electronics can handle repeated bending cycles without losing functionality. This design is especially beneficial when treating irregular body surfaces or joint areas. The bandage-like form factor also helps maintain consistent contact pressure, a critical factor for uniform microneedle insertion and optical coupling. Because both drug delivery and phototherapy often require repeated applications over days or weeks, comfort and convenience play a pivotal role in ensuring patient compliance.

The light-emitting layer, microneedle array, sensor suite, and control system can be combined in different configurations to suit a given indication. For deeper targets, emitters centered near 830 or 940 nm may be used; for superficial targets, about 630 nm may suffice. The microneedle array can be formulated to deliver small molecules or biologics. In some embodiments, local optical stimulation is used with transdermal delivery to modulate immune or inflammatory responses in the treatment region.

An advanced sensor system can be included, measuring variables such as temperature, humidity, or local reflectance, to ensure that each therapy session remains safe and effective. For example, if a sensor detects an excessive rise in local skin temperature, the control module might reduce light intensity to prevent patient discomfort or thermal damage. Likewise, if microneedle penetration is deemed insufficient (identified by changes in impedance or signal reflectivity), the system might prompt the user to reposition the device or to apply slightly more pressure to achieve correct skin contact. These safeguards can reduce risk, especially in vulnerable or sensitive patient populations, such as the elderly or individuals with neuropathy who might not sense pain or skin damage.

The method of operation typically involves the following steps: (1) the device is positioned on the user's skin at the target site; (2) the microneedle array is brought into contact with the skin, causing partial or full penetration of the stratum corneum; (3) the user or practitioner initiates the light therapy session through an interface on the control module; (4) the power system then drives the light-emitting layer at the prescribed wavelength, intensity, and duration; (5) simultaneously, the microneedle array releases or facilitates transdermal diffusion of therapeutic agents. Depending on the application, the device may operate continuously for a set period or follow a pulsed regime. In certain cases, multiple sessions per day are advisable, with the patch replaced or recharged as needed. When the microneedles are dissolvable, the user discards the patch after each session, obviating the need for sterile disposal procedures for sharps. Alternatively, if a non-dissolvable microneedle design is selected, the array might be sanitized and reused multiple times, provided the substrate supports such an approach and sterility can be maintained.

From a manufacturing standpoint, the invention leverages established techniques in flexible electronics, microneedle fabrication, and photomedical device design. QLED or OLED layers can be fabricated through large-area printing or vacuum deposition methods on polymer substrates, followed by encapsulation steps that protect the active layers from moisture and mechanical stresses. The microneedle arrays can be formed separately and then attached to the substrate using adhesive layers that do not compromise optical or mechanical integrity. To scale production, methods such as micromolding and photo-polymerization can yield thousands of microneedle patches per batch. Quality assurance focuses on verifying consistent needle length, tip sharpness, and drug loading. The final assembly involves laminating the microneedle array onto or near the light-emitting region, integrating the power supply and control electronics, and performing final device encapsulation. Because each subcomponent uses known industrial processes, this integrated design is amenable to high-volume production with relatively moderate capital investment once prototypes have been validated.

The invention has particular relevance for neuropathic pain applications. Peripheral nerve injuries, for example, often manifest as complex pain syndromes with both nociceptive and neuropathic components. Conventional management might rely heavily on opioids or invasive nerve blocks, each of which carries risks and limitations. By contrast, a wearable patch that delivers localized anesthetics and anti-inflammatory medications, combined with photobiomodulation targeting neural repair pathways, could provide comprehensive relief with fewer side effects. Preliminary or preclinical studies suggest that PBM can downregulate pro-inflammatory cytokines, upregulate anti-inflammatory mediators, and potentially accelerate nerve regeneration. When combined with transdermal agents that block sodium channels or reduce cyclooxygenase-mediated inflammation, the overall analgesic effect can be more potent and more targeted than any single modality alone.

In the dermatological and cosmetic domain, enhanced collagen remodeling and improved transdermal absorption of active agents can yield improved results compared to typical standalone treatments. Wrinkle reduction, improvement in skin texture, and mitigation of hyperpigmentation are frequent goals in cosmetic practice. Employing microneedle arrays to deliver compounds like retinoids, peptides, or vitamin C derivatives can be made more effective when the underlying dermis is also stimulated by photobiomodulation. This combination not only improves the penetration depth of those compounds but also supports cellular activity within the skin. Similarly, many chronic wounds benefit from increased local perfusion and oxygenation, which PBM can facilitate, and from localized administration of antibiotics or growth factors that microneedles can provide. This synergy may be pivotal for individuals prone to poor healing, such as those with diabetes or peripheral vascular disease.

Vaccination and immunotherapy represent additional applications, wherein the microneedles can deliver antigens or immune modulators directly to antigen-presenting cells in the epidermis or dermis, while concurrent photostimulation may activate or enhance localized immune processes. This could allow dose sparing or lead to faster immune responses. Various photobiological studies have indicated that certain wavelength ranges can modulate dendritic cell or T-cell functions. In vaccination and immunotherapy contexts, aPDT may be used to locally reduce microbial burden or biofilms prior to, or in parallel with, antigen delivery Personalized medicine trends support the concept of adaptive therapy, in which the device's sensors collect patient-specific data, and the control system modifies parameters in response. A wearable patch that logs usage data, tracks local physiologic markers, and adjusts treatment accordingly can integrate into telemedicine frameworks. For example, a patient with chronic pain could apply the patch at home, with data automatically transmitted to a clinician who reviews trends over time and refines the protocol. If the system detects diminishing returns, the wavelength or drug dosage could be changed remotely. This model could shift pain or wound management from a clinic-centric paradigm to a more distributed model, enabling earlier interventions and potentially improving health outcomes.

The invention's form factor is amenable to diverse shapes and sizes. One version might be shaped as a circular patch for small target areas like the knee or elbow, whereas a strip configuration could be employed for linear coverage along the spine or post-surgical incisions. Another variant might extend to large flexible sheets that conform to the torso for burn wounds or widespread dermatologic conditions. The potential for customization also ensures that certain subpopulations—pediatric, geriatric, or immunocompromised patients—can utilize this platform with suitable modifications in drug concentration, needle length, and sensor thresholds.

This wearable therapeutic device combines a flexible light-emitting layer with a dissolvable or biodegradable microneedle array to enable concurrent photobiomodulation and transdermal delivery. A power and control module manages wavelength, irradiance, and timing, and may use sensor feedback to adjust dose. The device is suitable for neuropathic pain, wound care, dermatology, and other indications that benefit from localized drug delivery with controlled optical stimulation.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 1 is a schematic illustration of the QLED-microneedle patch concept, showing the integration of a flexible QLED (10) for photobiomodulation therapy (PBM) and the microneedle array (12) for non-opioid drug delivery. The diagram also depicts application of the patch in a rat spared nerve injury model for preclinical testing.

DETAILED DESCRIPTION OF THE INVENTION

For a fuller understanding of the present invention, reference should be made to the following detailed description, taken in connection with the accompanying FIGS. 1-7, which illustrate the structure, function, and operation of a wearable therapeutic system that unifies photobiomodulation therapy and microneedle-mediated transdermal drug delivery. The system's core elements include a flexible substrate bearing a light-emitting layer, a microneedle array integrated on or near that same light-emitting layer, a control and power module, and an optional reservoir and sensor setup for advanced monitoring. By combining these features into a single patch or bandage, the invention achieves simultaneous or sequential photobiomodulation therapy and targeted drug administration across a wide range of medical and cosmetic applications, including neuropathic pain management, wound healing, skin rejuvenation, and inflammatory conditions.

The device's foundation is a flexible substrate selected to balance mechanical integrity with patient comfort. Various biocompatible polymers can be employed, such as polyethylene terephthalate, polydimethylsiloxane, or composites fortified with moisture barriers. The choice of substrate depends on whether the primary application is short-term disposable use or a more durable, reusable patch. In either case, the substrate is designed to conform to curved or irregular skin surfaces with minimal discomfort while maintaining sufficient rigidity to support the light-emitting layer and microneedles. As shown in FIG. 1, the substrate is typically integrated into a bandage-like form (14), which is placed onto the treatment area. Flexible edges, adhesives, or wrap-around fasteners may be incorporated to ensure consistent contact over the targeted location, whether that is the lower back, a limb, or the face. This conformable design is especially advantageous for patients requiring extended therapy sessions, as it can be worn with minimal disruption to daily activities.

Figure 2A:
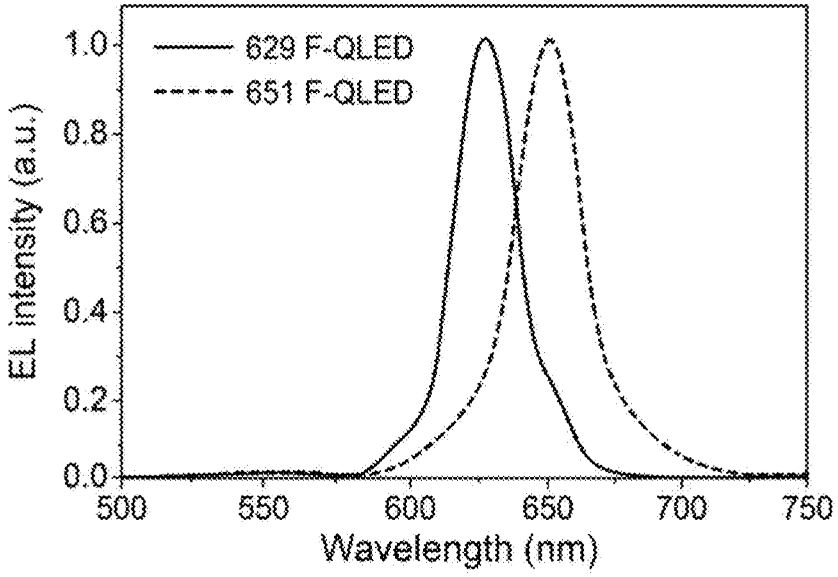
FIG. 2 is a graphical representation of the QLED device illustrating a) wavelength tunability and b) electroluminescence (EL) homogeneity, ensuring consistent therapeutic light output. The standard deviation (S.D.) of the emitted wavelengths is also shown, highlighting the device's ability to maintain precise spectral properties.
Figure 2B:
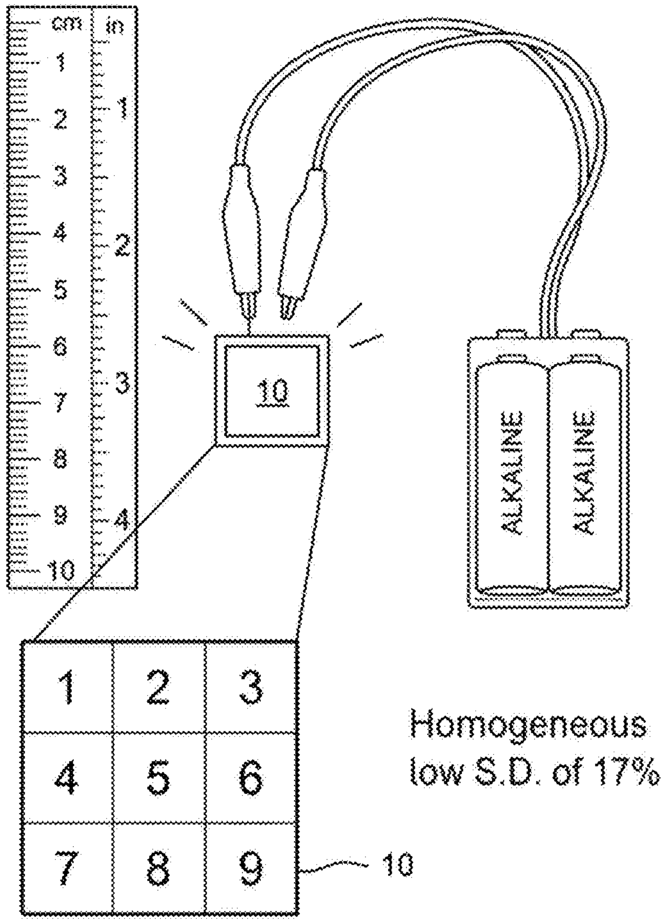
Figure 3A:
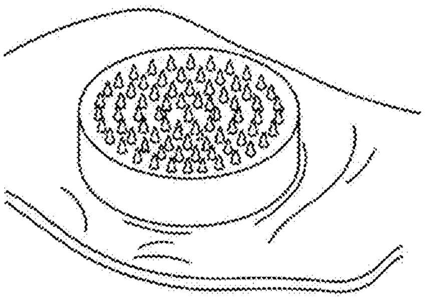
FIG. 3 is a set of optical and scanning electron microscope (SEM) images of the microneedle array (12), particularly those made from PEGDA. The images include A-C) microneedle curvature (~20 μm radius), D-E) ex vivo penetration into dermatomed human skin, and F) stimuli-responsive drug release behavior due to variations in temperature and pH. The data demonstrate the "intelligent" drug release mechanism enabled by the microneedle system.
Figure 3C:
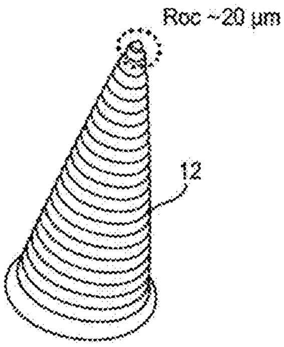
Figure 3B:
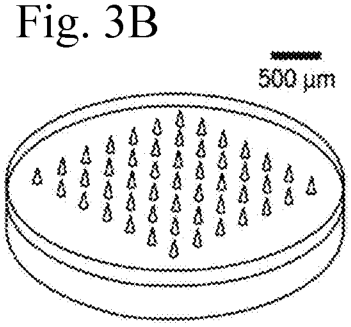
Figure 3D:
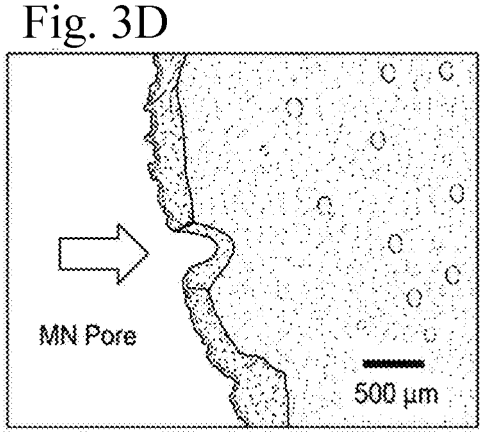
Figure 3E:
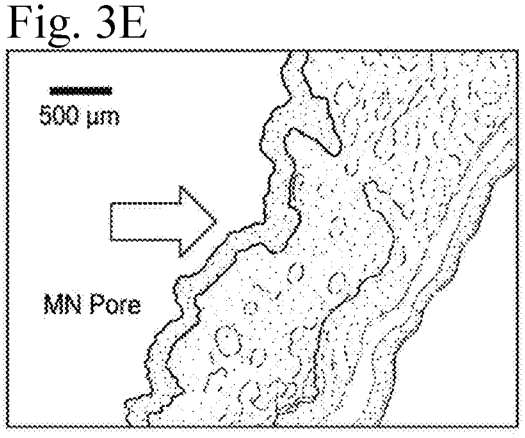
Figure 3F:
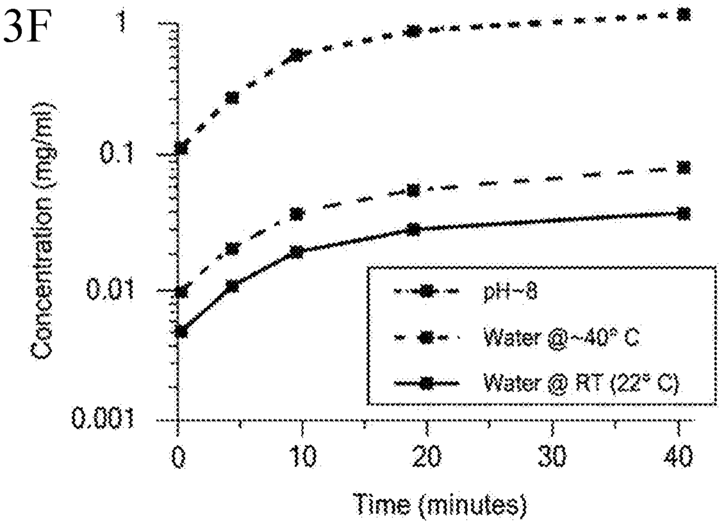
Figure 6:
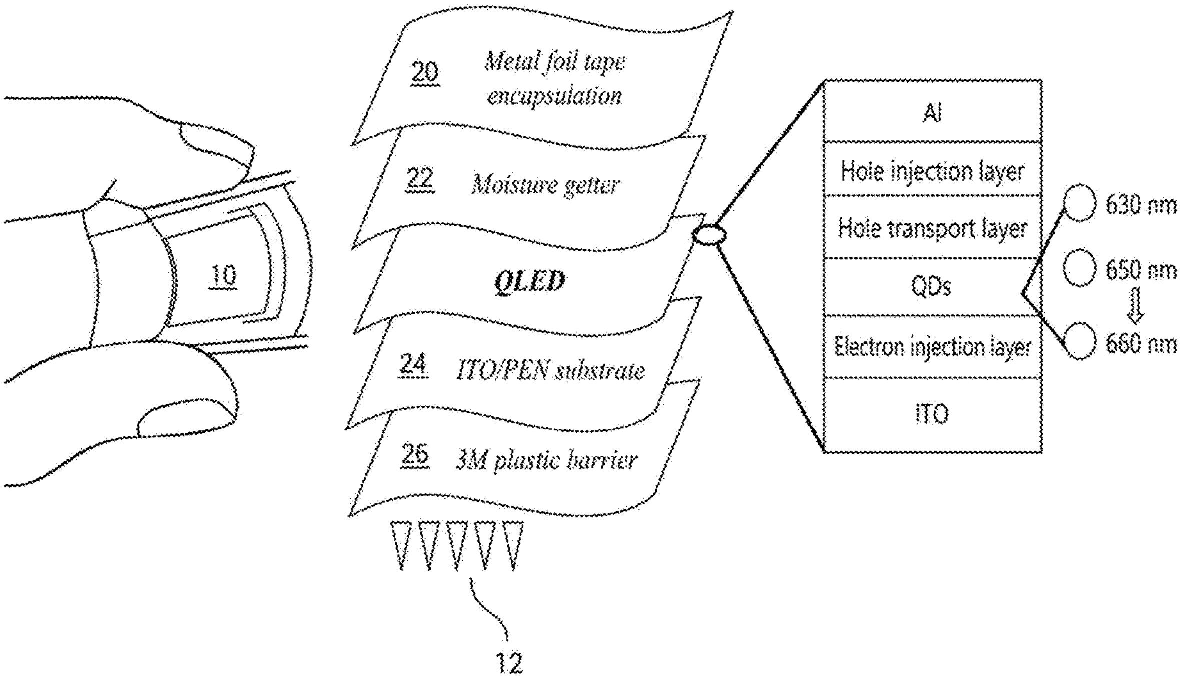
FIG. 6 is an exploded schematic of a flexible emitter-microneedle package. From top to bottom the stack can include a metal foil tape encapsulation (20), a moisture getter (22) disposed within the sealed volume, an emitter (10) carried on a transparent-conductor polymer substrate (24), for example an indium tin oxide coated polyethylene naphthalate (ITO/PEN) film, and an optional plastic barrier film (26) adjacent the microneedle array (12). The inset at right depicts a representative emitter stack with charge-injection and transport layers and selectable emission peaks, for example near 630 nm, 650 nm, or 660 nm.

On top of or within this flexible substrate lies a light-emitting layer configured for photobiomodulation (PBM) therapy. FIGS. 2 and 6 illustrate different embodiments of this layer, which can be based on quantum dot light-emitting diodes (QLEDs), organic light-emitting diodes (OLEDs), or traditional light-emitting diodes (LEDs). The QLED or OLED configurations offer key advantages such as low heat output, uniform areal emission, lightweight construction, and the possibility of precise wavelength tuning. For example, quantum dots of different sizes can be embedded to achieve specific emission peaks in the red, near-infrared, or even shorter visible wavelengths (e.g., blue or green) if particular applications require them. The spectral tuning can cover ranges of approximately 600-670 nm for wound healing and skin rejuvenation, 780-940 nm for deeper penetration to address pain in musculoskeletal tissues, and up to 1064 nm for enhanced reach into muscle or neural structures. Alternatively, shorter wavelengths around 400-590 nm can be employed for antimicrobial effects, acne treatment, or specific neurological photobiomodulation protocols. The device's control module (shown schematically in FIG. 7) adjusts not only wavelength but also intensity, duration, pulsation frequency, and treatment sequences, allowing a single device to address multiple indications.

As shown in FIG. 6, certain embodiments package the flexible light-emitting device 10 and the microneedle array 12 within a multilayer stack configured to manage moisture ingress and mechanical durability while preserving optical output. In one non-limiting arrangement, the package includes a metal foil tape encapsulation 20, a moisture getter 22 within the sealed volume, an emitter 10 formed on a transparent-conductor polymer substrate 24 such as an ITO-coated PET or PEN film, and an optional plastic barrier film 26 on the microneedle side of the assembly.

The metal foil tape encapsulation (20) can be an aluminum or other metal foil laminate having a pressure-sensitive or heat-activated adhesive. Encapsulation (20) may cover the periphery and edges of the emitter region to provide a low water-vapor transmission rate, and may define an optical aperture aligned with the active area of device (10). Edge sealing, perimeter rings, and overlapped segments are all contemplated.

The moisture getter (22) denotes any moisture-scavenging or oxygen-scavenging material positioned inside the encapsulated volume to extend emitter lifetime. Getter (22) may be provided as a discrete insert, a coated film, or a thin-film deposit, and can be positioned between encapsulation (20) and emitter (10) as shown, or elsewhere within the sealed cavity.

The substrate (24) supports the emissive stack and provides a transparent electrode. Suitable implementations include indium tin oxide on polymeric films such as PET or PEN, although other transparent conductors may be used. The optional plastic barrier film (26) may be a multilayer polymer barrier that further reduces moisture diffusion toward the microneedle side and provides a smooth bonding surface for array (12). Films (20), (22), (24), and (26) can be used in any operative order or combination compatible with optical transmission and device reliability.

The inset of FIG. 6 schematically illustrates a representative emitter stack for device (10), which can include one or more charge-injection and charge-transport layers on the transparent electrode, a quantum-dot emissive layer, and a top electrode. Emission wavelength can be selected or tuned, for example to about 630 nm, 650 nm, or 660 nm for PBM applications, without limiting the broader ranges already described.

To power the light-emitting layer, a flexible battery (16) or external power source is included within the same bandage or connected via a flexible printed circuit (FPC) connector (18). This power supply is selected to deliver sufficient energy for the typical therapeutic session (e.g., from 10 minutes to multiple hours), without adding excessive bulk or weight. In certain embodiments, a thin-film lithium-ion or lithium-polymer battery is laminated onto the substrate, ensuring comfort and maintaining the device's profile. The power module often contains onboard electronics that regulate current and voltage, enabling precise control of irradiance levels. Additionally, the system can include a user interface-ranging from a simple push button to a touchscreen or wireless link-so that clinicians or patients can choose specific treatment parameters. The device may be pre-programmed for common protocols (for instance, a set 630 nm PBM routine for 20 minutes), or fully configurable for advanced users who wish to fine-tune dosage and modulation patterns.

Figure 4A:
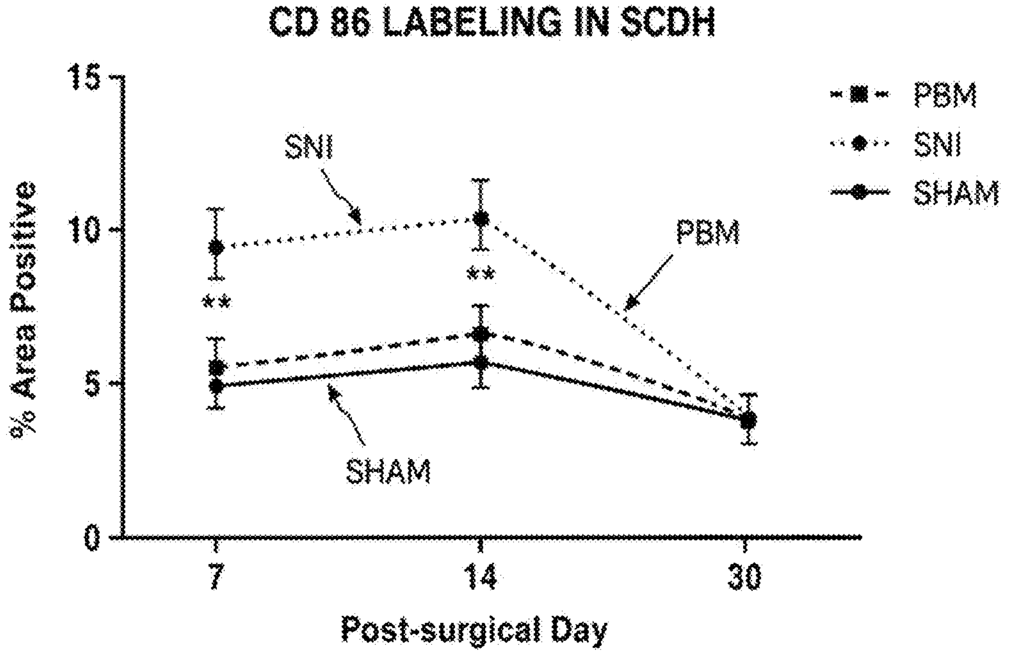
FIG. 4 is a bar graph illustrating the effect of PBMT on M1 marker expression in a spared nerve injury (SNI) model. The graph shows that SNI increased M1 marker CD86 expression in both the spinal cord dorsal horn (SCDH) at 7 and 14 days post-injury, and in the spinal cord dorsal column (SCDC) at 14 and 30 days post-injury. Notably, the elevation was not observed in animals that received PBM treatment.
Figure 4B:
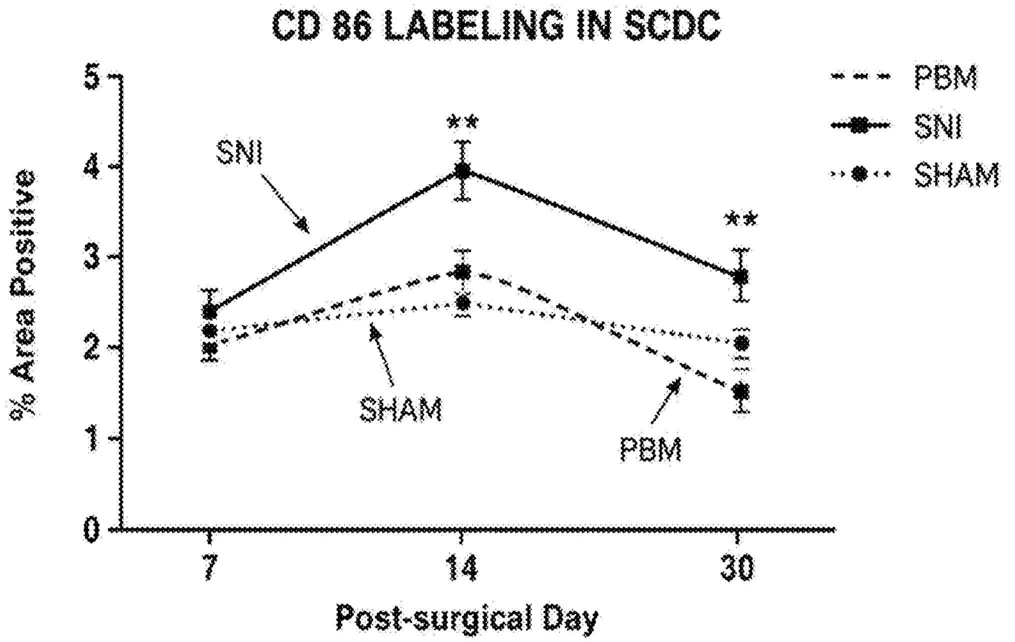
Figure 5:
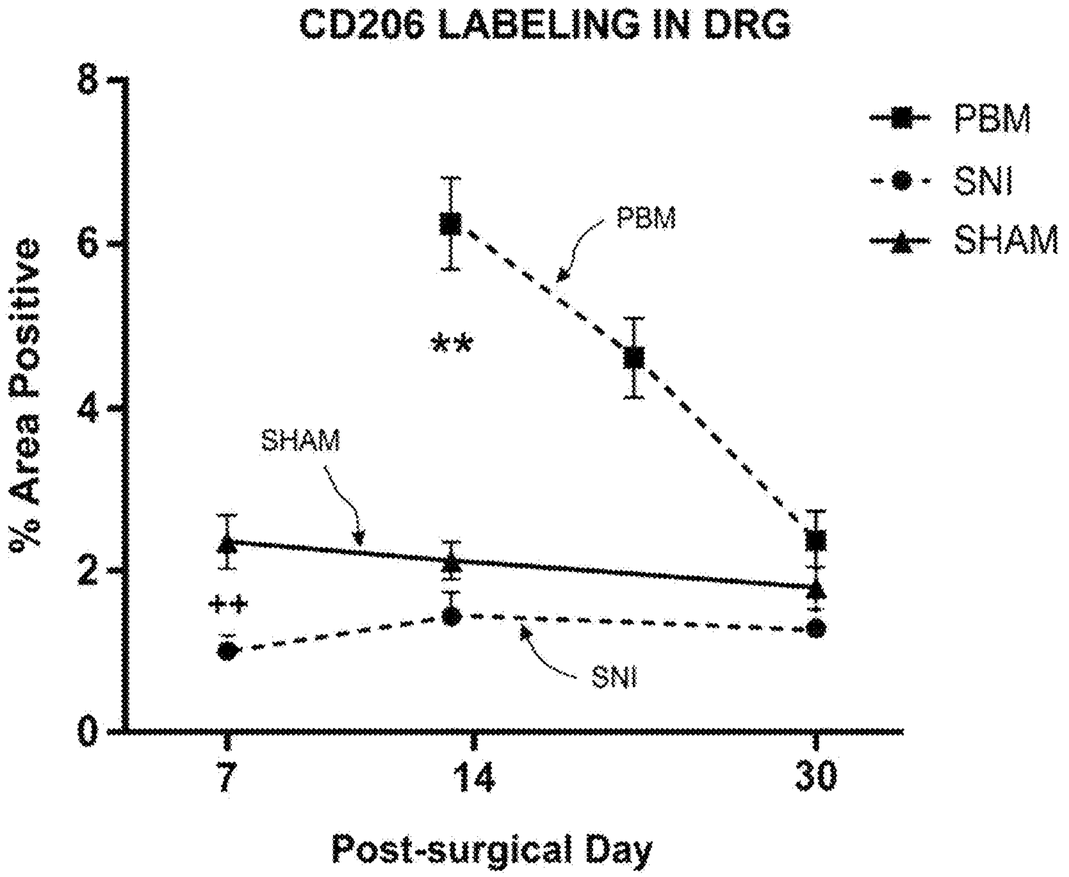
FIG. 5 is a bar graph illustrating the effect of PBMT on M2 marker expression in the SNI model. The data show that PBM increased M2 marker CD206 expression in comparison to both sham and untreated SNI groups at 14 and 30 days post-injury, indicating a shift toward an anti-inflammatory response.

The light output from the QLED or OLED layer is harnessed to stimulate biological processes conducive to healing and analgesia. Photobiomodulation in the red-to-NIR range is well established to enhance mitochondrial function by increasing cytochrome c oxidase activity, boosting ATP production, and regulating inflammatory signaling. FIGS. 4 and 5 show that application of light therapy in animal models leads to measurable shifts in immune marker expression (e.g., downregulation of M1 inflammatory markers such as CD86, and upregulation of M2 markers such as CD206). These immunomodulatory effects are particularly useful for neuropathic pain conditions (including peripheral nerve injuries or diabetic neuropathies), where local inflammation perpetuates chronic pain signaling. The same photobiological mechanisms are relevant for wound healing, as PBM can stimulate collagen synthesis, promote angiogenesis, and reduce edema. Likewise, in cosmetic settings such as skin rejuvenation or pigmentation correction, the device's light therapy component can address dermal remodeling and melanocyte regulation.

Example 1: SNI Rat Model Protocol

A preclinical protocol was executed in a spared nerve injury (SNI) rat model to evaluate the safety and efficacy of the flexible light-integrated microneedle device for pain modulation and localized drug delivery. Randomization and blinded assessments were employed throughout.

Animals and Group Assignment

A total of 168 two-month-old Sprague Dawley rats were allocated to 12 experimental or control groups, n=12 per group comprising 6 males and 6 females. An additional 24 rats were available for device checkout and to replace animals euthanized for autophagia.

Surgery

SNI or sham surgery was performed under isoflurane anesthesia. Through a lateral thigh incision, the tibial and common peroneal nerves were ligated and transected distal to the ligations, while the sural nerve was left intact to create neuropathic hypersensitivity in the ipsilateral dermatome. Musculature and skin were closed in layers with absorbable materials as described.

Device Application and Optical Dose

A 1 $cm^2$ flexible QLED-microneedle patch was adhered to shaved skin over the sciatic notch ipsilateral to the injury unless indicated. The QLED surface irradiance was tuned between 3 and 10 $mW/cm^2$, and irradiance delivered to the sciatic nerve was verified in anesthetized animals at selected surface settings.

Therapeutic Agents and Doses

Groups received microneedle-delivered meloxicam 2 mg/kg or ropivacaine 3 mg/kg, either as drug-only conditions, combined with light, or contrasted with subcutaneous injections of the same drugs without a device, as detailed in Table 1.

Behavioral Assessments

Blinded assessments encompassed an electronic von Frey test for mechanical allodynia, a heat hyperalgesia test, and a place escape/avoidance paradigm to quantify aversive behavior. Assessments were performed at 4 hours, 24 hours, and 3, 5, and 7 days following treatment initiation.

Sample Collection and Biomarkers

On day 8 after the start of treatment, animals were euthanized with perfusion for tissue histology; blood collected by cardiac puncture was analyzed on a Luminex platform for cytokines including IL-6, IL-1$\alpha$, IL-1$\beta$, TNF-$\alpha$, TGF-$\beta$, and IL-10. Skin, sciatic nerve, and adjacent skeletal muscle underlying the patch site were processed for morphology.

Statistics

Behavioral endpoints were summarized as mean±SEM and analyzed with two-way ANOVA across time, applying Bonferroni-Holm adjustments for multiple comparisons; cytokine and histology data were analyzed by ANOVA with appropriate post hoc tests at $\alpha$=0.05.

TABLE 1

Experimental groups, rat counts, assessment schedule, and euthanasia timing.

| Experimental Groups | Rat Number | Behavior Assessment | Euthanasia Sample Collection |
|---|---|---|---|
| SNI + QPAD Light Only | 12 (6 males + 6 females) | 4 and 24 hours and 3-, 5-, and 7-days post start of treatment | Day 8 post start of treatment |
| SNI + QPAD Meloxicam Only 2 mg/kg | 12 (6 males + 6 females) | 4 and 24 hours and 3-, 5-, and 7-days post start of treatment | Day 8 post start of treatment |
| SNI + QPAD Ropivacaine Only 3 mg/kg | 12 (6 males + 6 females) | 4 and 24 hours and 3-, 5-, and 7-days post start of treatment | Day 8 post start of treatment |
| SNI No Device Ropivacaine SQ Injection | 12 (6 males + 6 females) | 4 and 24 hours and 3-, 5-, and 7-days post start of treatment | Day 8 post start of treatment |
| SNI No Device Meloxicam SQ Injection | 12 (6 males + 6 females) | 4 and 24 hours and 3-, 5-, and 7-days post start of treatment | Day 8 post start of treatment |
| SNI + QPAD Light and Meloxicam | 12 (6 males + 6 females) | 4 and 24 hours and 3-, 5-, and 7-days post start of treatment | Day 8 post start of treatment |
| SNI + QPAD Light and Ropivacaine | 12 (6 males + 6 females) | 4 and 24 hours and 3-, 5-, and 7-days post start of treatment | Day 8 post start of treatment |
| SNI + No treatment | 12 (6 males + 6 females) | 4 and 24 hours and 3-, 5-, and 7-days post start of treatment | Day 8 post start of treatment |
| SNI + QPAD Light and Meloxicam placed over sciatic notch on non-injured sciatic nerve | 12 (6 males + 6 females) | 4 and 24 hours and 3-, 5-, and 7-days post start of treatment | Day 8 post start of treatment |
| SNI + QPAD Light and Ropivacaine placed over sciatic notch on non-injured sciatic nerve | 12 (6 males + 6 females) | 4 and 24 hours and 3-, 5-, and 7-days post start of treatment | Day 8 post start of treatment |
| Sham Surgery + QPAD + light + Meloxicam | 12 (6 males + 6 females) | 4 and 24 hours and 3-, 5-, and 7-days post start of treatment | Day 8 post start of treatment |
| Sham Surgery + QPAD + light + Ropivacaine | 12 (6 males + 6 females) | 4 and 24 hours and 3-, 5-, and 7-days post start of treatment | Day 8 post start of treatment |

In some embodiments, the light-emitting layer maintains an emission peak stability within ±5 nm during a treatment session, and the delivered areal optical dose is uniform within ±10 percent over the active area.

Areal Uniformity and Dosage Stability

In one implementation the emitter exhibits luminance uniformity within ±5 percent and dosage consistency within ±10 percent across 12 measurement sites.

Mechanical and Thermal Targets

For a 1×1 cm emitter, the device mass is ≤2 g, the device withstands 1,000 bend cycles, and during one hour of operation the patch surface temperature remains at or below ambient+5° C.

Lot Verification

Each attribute can be verified on at least 10 patches or 5% of a manufactured lot, with re-testing upon design iteration.

The microneedle array (12), depicted in FIGS. 1, 3, and 6, is vital to the device's transdermal drug delivery capability. By piercing the stratum corneum with micrometer-scale projections, the array dramatically increases skin permeability, allowing therapeutic agents to diffuse into the dermis or upper subcutaneous layers. The microneedles are generally formed from dissolvable or biodegradable polymers such as polyethylene glycol diacrylate (PEGDA), polyvinylpyrrolidone (PVP), or silk fibroin. In many embodiments, the needles themselves carry the active pharmaceutical ingredient—be it a local anesthetic (e.g., ropivacaine), an anti-inflammatory drug (e.g., meloxicam), a cosmetic formulation, or a biologic agent—such that once inserted, they dissolve over minutes to hours, releasing the agent at a controlled rate. FIG. 3 shows examples of polymer microneedles with a radius of curvature (~20 μm) optimized for minimal insertion pain while maintaining mechanical strength. In ex vivo penetration tests on dermatomed human skin, these microneedles create uniform micropores that facilitate more efficient diffusion of drugs compared to typical topical creams or ointments. The data in subfigure F of FIG. 3 demonstrate that the needle dissolution and drug release can be stimulus-responsive, potentially allowing for temperature-dependent or pH-dependent release profiles.

In some variations of the invention, a drug reservoir is included in fluid communication with the microneedle array. This reservoir can take the form of a small pouch or a microfluidic channel that dispenses medication into or onto the base of the microneedles. With suitable pumps or valves, drug delivery can be precisely timed or triggered, perhaps in synergy with the activation of the light-emitting layer. Such synergy may enhance therapeutic outcomes: photobiomodulation can increase local blood circulation and tissue permeability, while microneedles ensure that analgesic, anti-inflammatory, or regenerative compounds reach their intended targets. For instance, in cases of chronic neuropathic pain, the local environment's permeability to ropivacaine may be boosted by PBM, thus requiring a lower drug dose to achieve the same or better analgesic effect.

Figure 7:
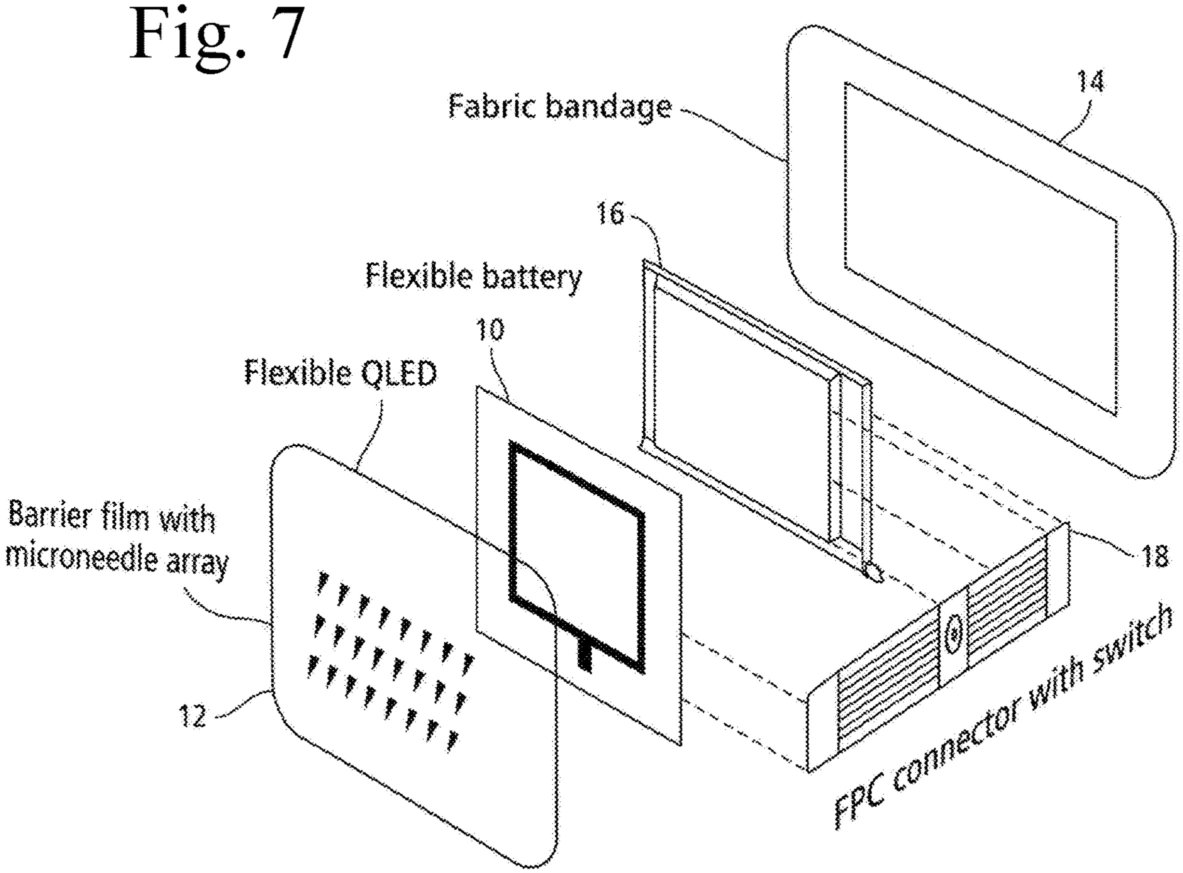
FIG. 7 is an exploded schematic of a wearable Q PAD system prototype that integrates the flexible QLED (10), microneedle array (12), bandage (14) for securing the device, flexible battery (16), FPC connector (18) for power and signal interfacing with control electronics, a sensor system (28) and a drug reservoir (30).

In addition to drug release, the microneedles offer an opportunity to introduce sensors. Some embodiments embed miniaturized electrodes or optical detection elements in or around the microneedle array, enabling real-time monitoring of skin impedance, tissue oxygenation, or drug concentration gradients. FIG. 7 sketches how sensors can be integrated into the overall patch design, transmitting data through the flexible printed circuit connector to the onboard control module or an external device. The resulting closed-loop system can adapt the PBM dosage or drug release in response to measured parameters. For example, if sensor readings indicate that skin temperature or inflammatory biomarkers have decreased to a threshold, the device can automatically reduce the light dose or slow drug delivery to prevent overtreatment. Conversely, if the patient's pain markers remain elevated, the system could increase dosage parameters within preset safety limits. As further shown schematically in FIG. 7, the device may optionally include a sensor system (28) operably coupled to the control electronics for monitoring one of more treatment parameters, and a drug reservoir (30) in fluid communication with the microneedle array (12) for storing and releasing a therapeutic agent.

Operation of the device typically begins by applying the patch to the target area after cleaning the skin. Because of the flexible substrate and integrated bandage material, the patch conforms to the curvature of the site, ensuring both effective optical contact and microneedle insertion. Once applied, the user or a healthcare provider can activate the device's power module, initiating the phototherapy session. If drug delivery is part of the prescribed regime, the microneedles simultaneously begin releasing medication. In certain modes, the light therapy may precede drug release to prime the tissue, or the system may alternate between phases of illumination and rest, controlling local blood flow or immune activity in a manner that complements the pharmacodynamics. This approach can be especially beneficial for pain management in peripheral neuropathies, where repeated or pulsatile PBM sessions modulate nerve signaling pathways while the microneedles maintain localized analgesic levels.

In aPDT modes, the method may include: loading a photosensitizer into microneedles or a reservoir; applying the patch to the target site; allowing a dwell period to equilibrate the photosensitizer locally; illuminating at a wavelength matched to the photosensitizer absorption for a selected fluence; optionally monitoring photobleaching or reflectance changes and adjusting light delivery accordingly; and removing or replacing the patch. Typical optical power densities can range from about 5 to about 25 $mW/cm^2$ and fluences from about 5 to about 100 $J/cm^2$, depending on indication and tissue type.

As the patch continues to operate, the control module, placed either locally on the patch or externally connected, manages parameters such as light intensity, wavelength cycling, drug reservoir flow rates, and microneedle dissolution profiles if the microneedle array is formulated to degrade over time. Once the treatment cycle completes—ranging from a few minutes to multiple hours—the patch can be removed and discarded if it is a single-use design (e.g., dissolvable microneedles) or recharged/refilled if it is a reusable system with a durable microneedle platform and a replaceable drug cartridge. In either scenario, the integrated electronics can store usage and compliance data for subsequent analysis. This tracking feature is invaluable for documenting a patient's progress, adjusting therapy parameters in multi-week or multi-month treatment regimens, and verifying that correct dosage was delivered at each session.

In terms of safety, the invention addresses several concerns prevalent in separate light therapy and transdermal drug administration systems. First, the patch uses low-level photonic energy in the range commonly recognized for PBM, which is generally safe and non-ablative. Built-in control circuits maintain the irradiance below hazardous thresholds, and the flexible substrate dissipates heat effectively, minimizing the risk of thermal injuries. Second, the microneedle array's dissolvable composition avoids the complications that can arise from retaining used needles or sharps, thereby reducing infection risk. Third, real-time monitoring of tissue responses (e.g., temperature sensors or penetration depth sensors) can help detect any adverse reactions promptly. If the device measures an unexpected rise in local temperature, it can shut off or reduce the light output automatically. If the user experiences discomfort, they can remove the patch at any time. The synergy between these fail-safes ensures a high margin of safety even when administered at home. In certain embodiments, the control module constrains surface temperature to at or below about 41° C., or to no more than ambient plus 5° C., while achieving the target fluence.

The device's applicability spans various fields. In neuropathic pain management, combining PBM and local drug delivery can target inflamed or damaged nerves, potentially expediting the restoration of normal nerve conduction and reducing reliance on opioids. In wound healing, red and near-infrared light can speed the closure of chronic wounds, while growth factors or antimicrobial compounds can be released via the microneedles to prevent infection and foster tissue granulation. In skin rejuvenation, the patch can deliver peptides, vitamins, or cosmeceuticals into the dermis while simultaneously stimulating collagen with photobiomodulation. Even in immunological or vaccination applications, the patch could incorporate immunomodulators or vaccine antigens into its microneedle array, and the light therapy might further enhance immunological responses in local tissues. The modular nature of the invention, as depicted in the exploded views (see FIGS. 1 and 6), supports easy adaptation to these different indications. Researchers can interchange microneedle formulations, adjust light wavelengths, or modify reservoir compositions without altering the fundamental architecture of the device.

One notable advantage over stand-alone light therapy devices is the improved patient compliance. Traditional PBM devices can be bulky, rigid, and require time-consuming sessions under specialized lamps or laser systems. By adopting a thin, flexible design, the present invention grants the patient freedom of movement. They can continue daily activities—such as walking, working, or resting at home—while the therapy takes place unobtrusively. This approach significantly reduces the logistical barriers that often hinder frequent or prolonged PBM usage. For individuals with chronic conditions like diabetic neuropathy or persistent back pain, the ability to self-administer therapy as needed fosters a sense of autonomy and can greatly improve adherence.

Manufacturing methods for the invention draw upon established processes in flexible electronics and microneedle fabrication. QLED or OLED panels can be produced via roll-to-roll printing or batch-based deposition on plastic substrates. Microneedle arrays can be cast, molded, or 3D-printed, then integrated onto the substrate using low-temperature bonding or UV-curable adhesives that do not degrade the optical or mechanical properties of the light-emitting layer. Protective coatings or encapsulations may be included to shield the QLED from oxygen and moisture, extending the operational lifespan. Similarly, the battery and control electronics can be laminated or incorporated using standard flexible circuit assembly techniques. These proven industrial workflows can be scaled from small pilot runs for clinical trials to high-volume commercial production.

The system can also incorporate a range of operational modes, each tailored to specific therapeutic goals. In a light-therapy-only mode, the microneedles remain inert (or can be omitted entirely if no transdermal agent is needed). In a drug-delivery-only mode, the patch may still benefit from real-time sensor feedback but omit photobiomodulation if, for instance, the primary objective is delivering a biologic agent. The combined therapy mode, however, is the most clinically exciting. Here, photobiomodulation and drug delivery occur in tandem, harnessing potential synergistic effects. Studies have shown that PBM can enhance skin permeability and local circulation, thereby improving pharmacokinetics of topically or transdermally delivered medications. Conversely, microneedle penetration can reduce reflection or scattering of the applied light in superficial skin layers, enabling deeper light penetration. Together, these phenomena substantially boost the overall therapeutic outcome, as indicated by the anti-inflammatory shifts captured in FIGS. 4 and 5.

In certain advanced embodiments, the invention includes a sensor suite that monitors microneedle penetration depth by measuring changes in electrical impedance or optical scatter. This real-time data ensures correct application and can automatically fine-tune the patch's settings if, for example, incomplete penetration is detected. The sensor suite might also evaluate tissue hydration or temperature, which can be critical for reliably dissolving the microneedle tips. Data from these sensors feed into the device's control software, ensuring each session is optimized. For instance, if the local temperature increases beyond a preset threshold, the software can reduce the light intensity or pause therapy, preventing excessive heating. If the sensor suite reveals slow or incomplete dissolution of the microneedles, the reservoir or drug release schedule might be adjusted accordingly.

Overall, the disclosed system resolves many shortcomings of separate microneedle patches and phototherapy devices by merging their functionalities in a user-centric, wearable format. The synergy between photobiomodulation and localized drug release is particularly beneficial for neuropathic and inflammatory conditions, where pain and tissue damage often coincide with compromised blood flow and high local inflammation. Through carefully tuned light emission, dissolvable microneedles, robust sensor feedback, and an intelligently managed power supply, the device offers clinicians and patients an efficient, minimally invasive, and adaptable treatment modality. The figures provided not only illustrate the core components and their arrangement but also demonstrate the biological impact of PBM and microneedle-based interventions, offering evidence for the system's efficacy in modulating immune markers and accelerating tissue repair.

Its expanded wavelength range, covering red, near-infrared, and even shorter or longer wavelengths, ensures a broad applicability across diverse medical and cosmetic indications. This versatility is critical in modern healthcare, where personalized therapies increasingly demand fine-grained control over treatment parameters. By including configurations for single or multi-wavelength output and optionally implementing cyclical or pulsed light sequences, the device meets the evolving needs of therapy protocols. In parallel, the microneedle array can be adapted to carry analgesics, anti-inflammatory drugs, growth factors, or cosmetic agents, each targeted to the desired tissue depth thanks to preselected microneedle geometries and dissolution rates. Taken together, these features make the disclosed system an important technological advance in integrated, wearable therapeutics that leverage the biological benefits of light at specific wavelengths while simplifying transdermal drug administration for enhanced healing, pain relief, and patient satisfaction.

Glossary of Claim Terms

Antimicrobial photodynamic therapy (aPDT) means a therapy using light, a photosensitizer, and oxygen to generate reactive species that reduce microbial load at a target site.

Barrier coating means a protective layer applied to the surface of a flexible substrate or other material to enhance durability, improve biocompatibility, and prevent environmental degradation. In the context of the therapeutic device, the barrier coating is essential for shielding the light-emitting components and microneedle array from moisture, mechanical stress, and biochemical interactions that may compromise device performance. Typically composed of thin-film polymers, silicone-based materials, or advanced nanocoatings, barrier coatings serve to prolong device lifespan while maintaining flexibility and transparency. In devices incorporating light-emitting layers such as quantum dot light-emitting diodes (QLEDs) or organic light-emitting diodes (OLEDs), the barrier coating plays a crucial role in preventing oxidation and degradation of the emissive layers. In microneedle applications, coatings ensure the stability of drug-loaded arrays, controlling dissolution rates for precise transdermal delivery. Additionally, specialized coatings can be designed to enhance adhesion between layered components, enabling stable device integration while minimizing interference with the therapeutic functions of the microneedles or light source.

Biocompatible polymer means a class of synthetic or naturally derived materials engineered for safe interaction with biological tissues without eliciting adverse immune responses. The flexible substrate and microneedle array of the therapeutic device employ biocompatible polymers to ensure structural integrity while enabling non-invasive or minimally invasive application. Common biocompatible polymers include polyethylene terephthalate (PET), polydimethylsiloxane (PDMS), polyethylene glycol diacrylate (PEGDA), and polyvinylpyrrolidone (PVP), which exhibit excellent mechanical properties, hydrophilicity, and bioinertness. In the flexible light-emitting layer, biocompatible polymers contribute to mechanical flexibility and conformability, enhancing patient comfort and ensuring consistent light delivery over irregular skin surfaces. In microneedle arrays, these polymers can be engineered for rapid dissolution, controlled drug release, or structural support, depending on the intended therapeutic application. Advanced polymer engineering techniques enable customization of properties such as biodegradability, permeability, and mechanical strength to optimize device performance while ensuring patient safety.

Composite material means a combination of two or more constituent materials that, when combined, exhibit enhanced mechanical, electrical, or biological properties beyond those of individual components. In the therapeutic device, composite materials are used for the flexible substrate, microneedle array, and barrier coatings to improve durability, flexibility, and biocompatibility. A composite material may integrate polymeric, metallic, or ceramic elements to enhance performance in medical applications. The use of polymer-based composites allows for tunable mechanical properties while ensuring safe interaction with human tissue. In microneedle applications, composite materials can enhance the strength and dissolution characteristics of biodegradable microneedles. In flexible light-emitting layers, composites may combine organic and inorganic components to optimize light emission and stability. The careful selection of composite materials enables multifunctionality within a single device, ensuring that it meets medical, cosmetic, and therapeutic requirements while maintaining patient comfort and safety.

Control module means an electronic system within the therapeutic device that regulates the power, duration, and intensity of emitted light, as well as the administration of transdermal therapeutic agents. The control module functions as the central processing unit, ensuring that the device operates according to pre-programmed treatment parameters or real-time sensor feedback. It manages the interaction between the power supply, light-emitting layer, and microneedle array to optimize therapeutic effectiveness. The module may include a microcontroller, wireless connectivity for remote control, and a user interface for adjusting settings. Advanced versions of the control module incorporate machine learning algorithms to personalize treatments based on patient response. It can also store and transmit treatment data, enabling healthcare providers to track therapy progress. The ability to fine-tune light wavelengths and energy output in response to skin conditions or therapeutic needs makes the control module a crucial component of the integrated system.

Drug reservoir means a storage compartment within the therapeutic device designed to hold and regulate the release of therapeutic agents through the microneedle array. The drug reservoir allows for precise dosing and sustained release, ensuring that therapeutic compounds reach targeted skin layers efficiently. It may contain liquid, gel, or solid drug formulations that are released upon activation of the microneedles or in response to external stimuli such as temperature, pH, or hydration. The reservoir is engineered with biocompatible materials to maintain drug stability and prevent degradation. In dissolvable microneedle applications, the drug reservoir can be integrated within the microneedle structure itself, releasing the active compound as the microneedles dissolve. For sustained-release therapies, the reservoir may incorporate hydrogel or polymeric matrices that modulate drug diffusion rates. This feature enhances the device's ability to deliver localized, controlled, and efficient transdermal therapy for a variety of medical and cosmetic applications.

Flexible substrate means a foundational layer within the therapeutic device that provides mechanical support while maintaining adaptability to conform to curved or irregular skin surfaces. The flexible substrate is a key component in ensuring comfort and effective treatment delivery in wearable medical devices. It is typically composed of biocompatible polymers such as polyethylene terephthalate (PET), polydimethylsiloxane (PDMS), or polymeric composites, which offer a balance of flexibility, durability, and transparency. The substrate serves as the base for integrating the light-emitting layer, microneedle array, and electronic components, facilitating their seamless operation. In light-emitting applications, the flexible substrate enhances the uniformity of light distribution while preventing mechanical strain on the device. In microneedle-based drug delivery, it ensures stable positioning of the microneedles for optimal penetration and sustained contact with the skin. By allowing the device to conform to the body's contours, the flexible substrate improves adherence and enhances the overall efficacy of therapeutic interventions.

Light-emitting diodes (LEDs) mean semiconductor devices that generate light through electroluminescence. In the therapeutic device, LEDs can deliver specific wavelengths optimized for photobiomodulation therapy (PBMT), antimicrobial photodynamic therapy (aPDT), wound healing, and transdermal drug enhancement. In some embodiments for PBMT, the device operates in the 630-660 nm range; in other embodiments the device is configured for broader ranges as otherwise described herein. The integration of LEDs into a flexible substrate enables wearable operation with controllable intensity and duration via the control module.

Light-emitting layer means a functional component in the therapeutic device responsible for generating and delivering specific wavelengths of light to targeted tissues. The light-emitting layer may incorporate quantum dot light-emitting diodes (QLEDs), organic light-emitting diodes (OLEDs), or conventional light-emitting diodes (LEDs), each offering unique advantages in spectral precision, energy efficiency, and flexibility. The emitted light operates within therapeutic ranges, such as red and near-infrared wavelengths, which are clinically proven to enhance cellular regeneration, reduce inflammation, and promote transdermal drug uptake. In addition to its therapeutic applications, the light-emitting layer is engineered for durability, ensuring stable light output over extended treatment sessions. The layer is integrated with the control module, allowing for dynamic adjustments in wavelength, intensity, and exposure time. When combined with a microneedle array, the light-emitting layer enhances drug permeability by increasing local tissue perfusion and cellular responsiveness, resulting in improved therapeutic outcomes.

Metal foil tape encapsulation means a sealing layer formed of metal foil or metallized polymer tape, typically with a pressure-sensitive or heat-activated adhesive, that covers at least a portion of the emitter package to reduce water-vapor transmission and oxygen ingress while providing mechanical protection. In some embodiments, the encapsulation (20) comprises aluminum foil, copper foil, stainless-steel foil, or a metallized polymer laminate. Encapsulation (20) may be continuous or patterned, may overlap at seams or edges, and can define an optical aperture aligned with the active emitting area of device (10). The encapsulation (20) can also contribute useful secondary functions such as thermal spreading, electromagnetic shielding, and edge sealing around through-vias or connectors. Thickness, adhesive type, and footprint are selected to balance barrier performance with flexibility so the device remains conformal when worn.

Microneedle array means a collection of micro-scale needles engineered for minimally invasive penetration of the skin to facilitate transdermal drug delivery. The microneedle array in the therapeutic device is designed to be integrated with the light-emitting layer, enabling combined phototherapy and drug administration. These microneedles may be composed of biodegradable polymers such as polyethylene glycol diacrylate (PEGDA), polyvinylpyrrolidone (PVP), or silk fibroin, which dissolve upon application, releasing therapeutic agents in a controlled manner. The microneedles are fabricated to precise lengths and geometries to ensure effective skin penetration without causing significant discomfort or damage. When used in conjunction with therapeutic light, the microneedle array enhances drug absorption by temporarily disrupting the skin barrier and increasing local circulation. This integration allows for a synergistic approach to treatment, maximizing the efficacy of both photobiomodulation therapy and transdermal drug delivery.

Moisture getter (22) means a moisture- and optionally oxygen-scavenging material, film, coating, or insert disposed within an encapsulated volume of the device to protect moisture-sensitive components of the light-emitting stack. In the context of the therapeutic device, the moisture getter (22) cooperates with encapsulation layers to establish a dry micro-environment that extends emitter lifetime, maintains optical output stability, and preserves adhesive performance. The getter (22) may be provided as a discrete die-cut patch, a laminated desiccant film, a printed or deposited thin film, or particles embedded within an adhesive layer. Non-limiting examples include calcium oxide, barium-aluminum alloys, zeolites, silica gel, molecular sieves, polymeric desiccant laminates, or other reactive or sorptive chemistries. The moisture getter (22) can be positioned beneath a metal foil tape encapsulation (20), above a transparent-conductor polymer substrate (24), integrated into an optional barrier film (26), or otherwise located within the sealed cavity without obstructing the optical aperture. Form factor, loading, and placement are selected to achieve the desired in-package water-vapor and oxygen levels over the intended service life of the patch.

Photobleaching signal means a change in photosensitizer optical absorption or emission during illumination that indicates dose delivery and can be used for feedback control.

Photobiomodulation therapy means a non-invasive therapeutic approach that uses specific wavelengths of light to modulate cellular function, enhance tissue repair, and reduce inflammation. In the context of the therapeutic device, photobiomodulation therapy (PBMT) is achieved using a light-emitting layer that delivers light in the red to near-infrared spectrum, typically between 630 nm and 660 nm for skin-related applications and up to 1064 nm for deeper tissue penetration. PBMT is based on the principle that mitochondria, specifically the enzyme cytochrome c oxidase (CCO), absorb certain wavelengths of light, leading to increased production of adenosine triphosphate (ATP), the primary energy source for cellular functions. This process enhances cellular metabolism, improves microcirculation, and accelerates healing. The therapeutic device integrates PBMT with a microneedle array, enhancing drug absorption by increasing skin permeability and stimulating biological responses that complement pharmacological treatment. The power supply and control module regulate PBMT parameters, ensuring precise dosage, duration, and intensity of light exposure based on the patient's condition. PBMT is widely applied in pain management, wound healing, muscle recovery, and neurological rehabilitation, making it a versatile and effective modality for various medical and cosmetic treatments.

Photosensitizer means a light-activatable compound that, in the presence of oxygen and light of a suitable wavelength, produces reactive molecular species that inactivate microbes.

Polyethylene glycol diacrylate means a biocompatible polymer commonly used in the fabrication of dissolvable microneedles and hydrogel-based drug delivery systems. As a photopolymerizable material, polyethylene glycol diacrylate (PEGDA) offers precise control over mechanical properties, dissolution rates, and drug release profiles. In the therapeutic device, PEGDA is used as a structural component of the microneedle array, enabling the fabrication of biodegradable microneedles that disintegrate upon skin penetration, releasing therapeutic agents in a controlled manner. The polymer's hydrophilic nature facilitates rapid dissolution, allowing for efficient transdermal drug delivery without the need for additional removal procedures. PEGDA is also used in bioadhesive coatings, enhancing the adhesion of microneedles to the skin for improved drug retention. Its tunable properties make it suitable for a wide range of biomedical applications, including tissue engineering and regenerative medicine. By integrating PEGDA-based microneedles with a light-emitting layer, the therapeutic device enhances drug absorption while simultaneously delivering phototherapy, providing a synergistic approach to treatment.

Polyethylene terephthalate means a durable and flexible polymer widely used as a substrate material in medical and electronic applications. In the therapeutic device, polyethylene terephthalate (PET) serves as the flexible substrate that supports the light-emitting layer and microneedle array. PET is chosen for its excellent mechanical strength, transparency, and biocompatibility, making it an ideal material for wearable medical devices. Its resistance to moisture and chemical degradation ensures the longevity of the device, protecting the internal components from environmental exposure. The flexibility of PET allows the device to conform to the body's contours, ensuring consistent contact with the skin for effective light therapy and drug delivery. Additionally, PET can be coated with specialized barrier layers to enhance its properties, preventing oxidation and improving adhesion between integrated components. PET is also used in optical applications due to its clarity and minimal light scattering, ensuring that emitted light is efficiently transmitted to the treatment area. The use of PET as a flexible substrate enhances the device's functionality, enabling seamless integration of electronic and therapeutic components while maintaining comfort and durability.

Polydimethylsiloxane means a silicone-based polymer known for its biocompatibility, flexibility, and optical transparency. Polydimethylsiloxane (PDMS) is commonly used in biomedical applications due to its inert properties and ability to form conformal coatings. In the therapeutic device, PDMS is utilized as a flexible substrate material that supports the light-emitting layer and microneedle array. Its elasticity allows the device to adapt to body movements, maintaining consistent skin contact for optimal therapy delivery. PDMS also serves as a barrier coating, protecting the underlying components from moisture and mechanical stress. Due to its high optical clarity, PDMS ensures efficient transmission of therapeutic light, minimizing energy loss and maximizing treatment efficacy. In microneedle applications, PDMS-based molds are used to fabricate precisely structured microneedle arrays, enabling controlled drug release and penetration depth. The polymer's non-reactive nature makes it suitable for prolonged skin contact, reducing the risk of irritation or allergic reactions. PDMS is widely employed in microfluidics and bioelectronics, further expanding its potential applications in advanced medical devices. The integration of PDMS within the therapeutic device enhances durability, functionality, and patient comfort.

Polyvinylpyrrolidone means a water-soluble polymer frequently used in pharmaceutical formulations, biomedical coatings, and dissolvable microneedles. Polyvinylpyrrolidone (PVP) is selected for its excellent biocompatibility, film-forming properties, and controlled dissolution characteristics. In the therapeutic device, PVP is a primary material for the microneedle array, enabling the fabrication of dissolvable microneedles that deliver therapeutic agents transdermally before fully disintegrating. This eliminates the need for needle removal and enhances patient compliance. PVP can be tailored to achieve specific dissolution rates, allowing for immediate or sustained drug release depending on the therapeutic need. Additionally, PVP is used in bio-adhesive coatings, improving the adhesion of microneedles to the skin for more effective drug delivery. The polymer's ability to stabilize active pharmaceutical ingredients further enhances the efficacy of transdermal therapies. When combined with photobiomodulation therapy, PVP-based microneedles improve drug uptake by increasing skin permeability, resulting in a synergistic effect. PVP's safety, versatility, and controlled degradation make it an essential component in advanced drug delivery systems.

Power supply means the energy source that drives the therapeutic device, enabling the operation of the light-emitting layer and control module. The power supply in the device may consist of a rechargeable battery, wireless energy transfer system, or direct electrical connection, depending on the intended application. The power supply is designed to deliver a stable voltage and current to ensure consistent light emission and controlled microneedle activation. Advanced power management systems may incorporate energy-efficient circuits, allowing for extended operation without frequent recharging. Some configurations include wireless charging capabilities for enhanced convenience in wearable applications. The integration of the power supply with the control module enables dynamic modulation of treatment parameters, such as light intensity, wavelength selection, and treatment duration. The compact and lightweight design of the power supply ensures that the device remains portable and comfortable for long-term use. By providing a reliable energy source, the power supply ensures that photobiomodulation therapy and transdermal drug delivery are executed with precision and effectiveness.

Quantum dot light-emitting diodes mean a type of light-emitting device that utilizes quantum dots—nanoscale semiconductor particles—to produce highly efficient and tunable light emission. Quantum dot light-emitting diodes (QLEDs) offer significant advantages over traditional LEDs, including higher color purity, energy efficiency, and spectral stability. In the therapeutic device, QLEDs serve as the primary light-emitting layer, providing targeted wavelengths in the red to near-infrared range for photobiomodulation therapy. The unique properties of quantum dots allow precise tuning of emission spectra, optimizing therapeutic effects for wound healing, pain management, and enhanced drug absorption. Unlike conventional LEDs, QLEDs are flexible and can be integrated into a wearable form factor, ensuring consistent and uniform light exposure to the treatment area. The combination of QLEDs with a microneedle array enhances transdermal drug delivery by increasing local tissue perfusion and permeability. Additionally, QLEDs operate at lower temperatures, reducing the risk of thermal damage to the skin while maintaining therapeutic efficacy. The integration of QLEDs within the therapeutic device represents an advancement in medical photonics, enabling personalized and effective treatment solutions.

Sensor system means an integrated set of electronic and optical sensors within the therapeutic device that monitor and adjust treatment parameters in real time. The sensor system detects variables such as skin contact, light dosage, microneedle penetration depth, and treatment response. By providing continuous feedback, the sensor system allows the control module to dynamically adjust the intensity, duration, and wavelength of emitted light based on patient-specific needs. Advanced sensor configurations may include biosensors that analyze skin hydration, temperature, and biochemical markers to further personalize treatment. In wearable applications, the sensor system enhances safety by preventing overexposure to therapeutic light and ensuring proper microneedle placement. Data collected by the sensors can be stored and analyzed to track treatment progress, enabling healthcare providers to refine therapy protocols. The incorporation of a sensor system elevates the therapeutic device beyond traditional static treatments, making it an adaptive and intelligent medical solution.

Silk fibroin means a naturally derived biocompatible protein polymer obtained from the silk of the *Bombyx mori* silkworm, known for its exceptional mechanical strength, biodegradability, and compatibility with biological tissues. In the therapeutic device, silk fibroin is used as a structural material for microneedles due to its ability to form stable, dissolvable matrices that allow controlled drug release. When used in microneedle fabrication, silk fibroin can be engineered to dissolve at specific rates, ensuring the gradual delivery of therapeutic agents transdermally. Its stability at physiological conditions makes it an excellent carrier for sensitive bioactive compounds, including peptides, proteins, and small-molecule drugs, preserving their efficacy during storage and application. Additionally, silk fibroin's mechanical properties enable the formation of sharp, durable microneedles that penetrate the skin effectively without causing significant pain or tissue damage. Unlike synthetic polymers, silk fibroin degrades into amino acids that are naturally metabolized by the body, eliminating concerns about long-term biocompatibility or inflammatory responses. The use of silk fibroin in the therapeutic device enhances patient safety, improves drug stability, and supports the integration of advanced transdermal delivery mechanisms with photobiomodulation therapy.

Therapeutic agent means any pharmacologically active compound designed to provide medical benefits when delivered through the microneedle array of the therapeutic device. The therapeutic agent may include non-opioid analgesics such as ropivacaine for localized pain relief, anti-inflammatory drugs like meloxicam for reducing inflammation, or biologics such as growth factors for tissue regeneration. The integration of a therapeutic agent within the microneedle array allows for direct transdermal administration, bypassing first-pass metabolism and improving bioavailability. Therapeutic agents can be encapsulated in dissolvable microneedles composed of polyethylene glycol diacrylate (PEGDA), polyvinylpyrrolidone (PVP), or silk fibroin, ensuring controlled and sustained release upon application. The combination of photobiomodulation therapy with therapeutic agents enhances treatment efficacy by increasing cellular metabolism, improving drug absorption, and promoting localized healing. Advanced formulations may also include antimicrobial compounds for infection control, antioxidants for skin rejuvenation, or neuroprotective agents for nerve repair. The selection of a therapeutic agent is tailored to the specific medical or cosmetic application, ensuring precise, effective, and patient-friendly treatment outcomes.

Transdermal delivery means a method of administering therapeutic agents through the skin using microneedle arrays that create temporary microchannels, enhancing the absorption of bioactive compounds. Unlike conventional drug delivery methods such as oral administration or injections, transdermal delivery bypasses gastrointestinal degradation and hepatic first-pass metabolism, leading to improved drug bioavailability and reduced systemic side effects. In the therapeutic device, transdermal delivery is achieved through a microneedle array that penetrates the stratum corneum, facilitating the controlled release of therapeutic agents directly into the underlying skin layers. The dissolvable nature of microneedles made from polymers such as polyethylene glycol diacrylate (PEGDA), polyvinylpyrrolidone (PVP), or silk fibroin ensures that the drug payload is released gradually, providing sustained therapeutic effects. When combined with photobiomodulation therapy, transdermal delivery is further optimized by increasing skin permeability, stimulating local circulation, and enhancing cellular uptake of therapeutic compounds. This synergistic approach enables more efficient drug administration for conditions such as chronic pain, inflammation, wound healing, and dermatological disorders. The controlled nature of transdermal delivery minimizes discomfort and improves patient adherence, making it a preferred method for non-invasive medical and cosmetic treatments.

Transparent-conductor polymer substrate (24) means a flexible polymeric film bearing a transparent, electrically conductive layer that supports the emissive stack and functions as a transparent electrode. The transparent-conductor polymer substrate (24) can include indium tin oxide (ITO) on polyethylene naphthalate (PEN) or polyethylene terephthalate (PET), and may alternatively employ other transparent conductors such as indium zinc oxide, aluminum-doped zinc oxide, silver nanowires, graphene, or PEDOT: PSS. Substrate (24) provides mechanical support, optical transmission toward the microneedle array (12), and electrical interfacing to charge-injection layers of the emitter. Optional surface treatments or planarization and adhesion-promotion coatings can be included to improve film uniformity and layer adhesion. Substrate thickness, sheet resistance, and optical transmittance are selected to deliver uniform, areal emission while maintaining the bendability required for wearable use.

REFERENCE NUMERALS (10) Light-emitting device: flexible QLED, OLED, or LED emitter configured to generate therapeutic light for photobiomodulation.

(12) Microneedle array: collection of biodegradable or dissolvable microneedles for transdermal drug delivery.

(14) Bandage or patch carrier: flexible adhesive support structure that secures the device to the skin.

(16) Flexible battery: thin, rechargeable power source for the light-emitting layer and control electronics.

(18) Flexible printed circuit (FPC) connector: electrical interconnect that couples power and signals between the light-emitting device and the control module.

(20) Metal foil tape encapsulation: metal-foil laminate with adhesive that seals the emitter package and reduces water-vapor transmission while preserving flexibility.

(22) Moisture getter: moisture- and oxygen-scavenging film or insert within the encapsulated volume that protects the light-emitting stack from environmental degradation.

(24) Transparent-conductor polymer substrate: flexible polymeric film, for example an ITO-coated PEN or PET film, that serves as a transparent electrode and mechanical support for the emissive stack.

(26) Plastic barrier film: optional polymer barrier layer that limits moisture diffusion toward the microneedle side and provides a bonding surface for the microneedle array.

(28) Sensor system: one or more sensors operably coupled to the control electronics and configured to monitor one or more treatment parameters.

(30) Reservoir: a reservoir in fluid communication with the microneedle array for storing and releasing a therapeutic agent or photosensitizer.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A therapeutic device, comprising:

a. a flexible substrate comprising a transparent-conductor polymer substrate;

b. a light-emitting layer disposed on the flexible substrate, the light-emitting layer comprising quantum dot light-emitting diodes (QLEDs) or organic light-emitting diodes (OLEDs) providing substantially uniform areal emission over an emitter active area, being formed on the transparent-conductor polymer substrate, and configured to emit light at a therapeutic wavelength between approximately 630 nm and 660 nm;

c. a microneedle array disposed on or integrated with the light-emitting layer, wherein the microneedle array comprises microneedles that microneedles are configured to penetrate the epidermis and facilitate transdermal delivery of a therapeutic agent; and d. a power supply and control module operably connected to the light-emitting layer and configured to control intensity and duration and to select among two or more therapeutic wavelengths within the range recited in element (b).

2. The device of claim 1, wherein the flexible substrate comprises a biocompatible polymer selected from polyethylene terephthalate (PET), polyethylene naphthalate (PEN), or a composite material with a barrier coating to prevent moisture ingress.

3. The device of claim 1, wherein the microneedle array comprises microneedles made of polyethylene glycol diacrylate (PEGDA) and having a radius of curvature of about 20 μm.

4. The device of claim 1, wherein the microneedle array is disposed on the same side of the flexible substrate as the light-emitting layer, such that the microneedles penetrate the skin while the light-emitting layer is optically coupled to the treatment area, and a plastic barrier film is disposed adjacent the microneedle array.

5. The device of claim 1, further comprising a drug reservoir in fluid communication with the microneedle array, the drug reservoir configured to store and control the release of a therapeutic agent through the microneedles for sustained or on-demand delivery, including stimulus-responsive release triggered by temperature, pH, hydration, or illumination.

6. The device of claim 1, wherein the light-emitting layer is configured to deliver photobiomodulation therapy (PBMT) to enhance mitochondrial cytochrome c oxidase activity in peripheral nerve cells, reduce inflammation associated with peripheral nerve injuries, and improve drug absorption of a non-opioid analgesic or anti-inflammatory agent.

7. The device of claim 1, wherein the power supply and control module includes a rechargeable battery encased within a flexible enclosure and a user interface for selecting treatment parameters.

8. A therapeutic device, comprising:

a. a flexible substrate;

b. a light-emitting layer disposed on the flexible substrate, the light-emitting layer comprising quantum dot light-emitting diodes (QLEDs), organic light-emitting diodes (OLEDs), or light-emitting diodes (LEDs) configured to emit light at a therapeutic wavelength between approximately 600 nm and 1064 nm;

c. a microneedle array disposed on or integrated with the light-emitting layer, wherein the microneedle array comprises microneedles that are configured to penetrate the epidermis and facilitate transdermal delivery of a therapeutic agent; and d. a power supply and control module operably connected to the light-emitting layer and configured to modulate the intensity, duration, and wavelength of emitted light; and e. a sensor system operably coupled to the power supply and control module, the sensor system configured to monitor local temperature, total delivered light dose, and microneedle penetration depth based on tissue impedance or optical backscatter, wherein the power supply and control module is configured to adjust treatment parameters responsive to signals from the sensor system and to prompt repositioning of the device or increased contact pressure when complete microneedle penetration is detected.

9. The device of claim 8, wherein the light-emitting layer is configured to emit at least one wavelength selected from 780-940 nm for deep tissue repair and pain management and at least one wavelength selected from 950-1064 nm for enhanced penetration into muscle and neural tissues.

10. The device of claim 8, wherein the light-emitting layer is further configured to emit wavelengths in the 400-630 nm range, including blue, green, and yellow light, in a selectable multi-band configuration with at least one wavelength in the 630-670 nm or 780-940 nm range for antimicrobial applications, skin tone correction, or neurological photobiomodulation therapy.

11. The device of claim 8, wherein the power supply and control module is configured to alternate or combine multiple therapeutic wavelengths in a programmable sequence while maintaining homogeneous fluence over a treated area and controlling heat generated during treatment.

12. The device of claim 8, wherein the therapeutic agent comprises a photosensitizer selected from methylene blue, chlorin e6, or indocyanine green, and the light-emitting layer is configured to emit one or more wavelengths matched to the selected photosensitizer.

13. The device of claim 12, wherein the microneedle array:

is configured to encapsulate the photosensitizer agent; includes a coating of the photosensitizer agent; or is configured to carry the photosensitizer to the treatment site.

14. The device of claim 12, wherein the light-emitting layer is configured to emit within ±20 nm of a photosensitizer absorption peak for methylene blue at about 650-660 nm, chlorin e6 at about 660-670 nm, or indocyanine green at about 780-820 nm.

15. The device of claim 12, further comprising a reservoir in fluid communication with the microneedle array to supply the photosensitizer as a solution of hydrogel for sustained or on-demand delivery, including stimulus-responsive release triggered by temperature, pH, hydration, or illumination.

16. The device of claim 12, wherein the sensor system is configured to monitor photobleaching, diffuse reflectance, oxygenation, or temperature during aPDT, and the power supply and control module is configured to irradiance, duty cycle, wavelength selection, or treatment duration responsive to a monitored signal.

17. The device of claim 12, wherein the light-emitting layer is configured to emit within ±10 nm of an absorption peak of the photosensitizer for methylene blue e at about 650-660 nm, chlorin e6 at about 660-670 nm, or indocyanine green at about 780-820 nm.

18. The device of claim 8, wherein the microneedle array comprises dissolvable, coated, hollow, or solid microneedles selected according to a target release profile, the target release profile including microneedle length, tip diameter, spacing, or dissolution rate for a target body site or therapy objective.

19. The device of claim 8, wherein the power and control module constrains a maximum patch surface temperature to at or below about 41° C., or to no more than ambient plus 5° C., during treatment by adjusting intensity, duty cycle, or treatment duration responsive to local temperature measured by the sensor system.

20. The device of claim 8, wherein the light-emitting layer provides areal dose uniformity within ±10 percent over an emitter active area and emission peak stability within ±5 nm during treatment.

21. The device of claim 8, wherein the light-emitting layer is packaged with a metal foil tape encapsulation that defines an optical aperture aligned with an emitter active area and houses a moisture getter within a sealed volume, the light-emitting layer being formed on a transparent-conductor polymer substrate and a plastic barrier film being dispose ed adjacent the microneedle array.

* * * * *